(12) United States Patent
Hayashi et al.

(10) Patent No.: US 8,067,211 B2
(45) Date of Patent: Nov. 29, 2011

(54) METHOD FOR PRODUCTION OF L-GLUTAMINE

(75) Inventors: Mikiro Hayashi, Tokyo (JP); Masaki Maeda, Tokyo (JP); Yoshiyuki Yonetani, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 684 days.

(21) Appl. No.: 12/159,156

(22) PCT Filed: Dec. 27, 2006

(86) PCT No.: PCT/JP2006/326023
§ 371 (c)(1),
(2), (4) Date: Jun. 25, 2008

(87) PCT Pub. No.: WO2007/074857
PCT Pub. Date: Jul. 5, 2007

(65) Prior Publication Data
US 2010/0184163 A1 Jul. 22, 2010

(30) Foreign Application Priority Data
Dec. 27, 2005 (JP) ................................. 2005-373873

(51) Int. Cl.
*C12P 13/14* (2006.01)
*C12N 1/20* (2006.01)
*C07H 21/04* (2006.01)

(52) U.S. Cl. ..................... 435/110; 435/193; 435/252.3; 435/252.32; 536/23.2

(58) Field of Classification Search .................. 435/110, 435/193, 252.3, 320.1
See application file for complete search history.

(56) References Cited

U.S. PATENT DOCUMENTS

| 6,855,516 B1 | 2/2005 | Nagai et al. |
| 2003/0003550 A1* | 1/2003 | Nakamura et al. ............ 435/110 |
| 2003/0148474 A1 | 8/2003 | Gusyatiner et al. |

FOREIGN PATENT DOCUMENTS

| JP | 55-148094 | 11/1980 |
| JP | 03-232497 | 10/1991 |

OTHER PUBLICATIONS

Nolden, et al., "Glutamine synthetases of *Corynebacterium glutamicum*: transcriptional control and regulation of activity", FEMS Microbiology Letters, vol. 201 (2001) 91-8.
Jakoby, et al., "Nitrogen regulation in *Corynebacterium glutamicum*: isolation of genes involved and biochemical characterization of corresponding proteins", FEMS Microbiology Letters, vol. 173 (1999) 303-10.
Hirasawa, et al., "L-Glutamate production by lysozyme-sensitive *Corynebacterium glutamicum* ltsA mutant strains", BMC Biotechnology, vol. 1, No. 9 (2001).
Hirasawa, et al., "A Mutation in the *Corynebacterium glutamicum* ltsA Gene Causes Susceptibility to Lysozyme, Temperature-Sensitive Growth, and L-Glutamate Production", Journal of Bacteriology, vol. 182, No. 10 (2000) 2696-2701.

* cited by examiner

Primary Examiner — Tekchand Saidha
(74) *Attorney, Agent, or Firm* — Fitzpatrick, Cella, Harper & Scinto

(57) ABSTRACT

A polypeptide comprising an amino acid sequence in which one or more amino acids are deleted, substituted or added in the amino acid sequence of a glutamine synthetase 2 derived from a microorganism belonging to a coryneform bacterium, wherein the coryneform bacterium producing the polypeptide has L-glutamine productivity, a DNA encoding the polypeptide, a recombinant DNA comprising the DNA, a microorganism comprising the DNA or the recombinant DNA, and a process for producing L-glutamine using the microorganism are provided.

12 Claims, No Drawings

SEQUENCE LISTING

```
<160> NUMBER OF SEQ ID NOS: 16

<210> SEQ ID NO 1
<211> LENGTH: 446
<212> TYPE: PRT
<213> ORGANISM: Corynebacterium glutamicum ATCC13032

<400> SEQUENCE: 1

Met Asn Ser Glu Gln Glu Phe Val Leu Ser Ala Ile Glu Glu Arg Asp
  1               5                  10                  15

Ile Lys Phe Val Arg Leu Trp Phe Thr Asp Ile Leu Gly His Leu Lys
             20                  25                  30

Ser Val Val Ala Pro Ala Glu Leu Glu Ser Ala Leu Glu Glu Gly
         35                  40                  45

Ile Gly Phe Asp Gly Ser Ala Ile Glu Gly Tyr Ala Arg Ile Ser Glu
     50                  55                  60

Ala Asp Thr Ile Ala Arg Pro Asp Pro Ser Thr Phe Gln Val Leu Pro
 65                  70                  75                  80

Leu Glu Ala Gly Ile Ser Lys Leu Gln Ala Ala Arg Leu Phe Cys Asp
                 85                  90                  95

Val Thr Met Pro Asp Gly Gln Pro Ser Phe Ser Asp Pro Arg Gln Val
                100                 105                 110

Leu Arg Arg Gln Val Gln Leu Ala Ala Asp Glu Gly Leu Thr Cys Met
            115                 120                 125

Ile Ser Pro Glu Ile Glu Phe Tyr Leu Val Gln Ser Leu Arg Thr Asn
        130                 135                 140
```

```
Gly Leu Pro Pro Val Pro Thr Asp Asn Gly Gly Tyr Phe Asp Gln Ala
145                 150                 155                 160

Thr Phe Asn Glu Ala Pro Asn Phe Arg Arg Asn Ala Met Val Ala Leu
            165                 170                 175

Glu Glu Leu Gly Ile Pro Val Glu Phe Ser His His Glu Thr Ala Pro
        180                 185                 190

Gly Gln Gln Glu Ile Asp Leu Arg His Ala Asp Ala Leu Thr Met Ala
    195                 200                 205

Asp Asn Ile Met Thr Phe Arg Tyr Ile Met Lys Gln Val Ala Arg Asp
210                 215                 220

Gln Gly Val Gly Ala Ser Phe Met Pro Lys Pro Phe Gln Glu His Ala
225                 230                 235                 240

Gly Ser Ala Met His Thr His Met Ser Leu Phe Glu Gly Asp Thr Asn
            245                 250                 255

Ala Phe His Asp Pro Asp Asp Ser Tyr Met Leu Ser Lys Thr Ala Lys
        260                 265                 270

Gln Phe Ile Ala Gly Ile Leu His His Ala Pro Glu Phe Thr Ala Val
    275                 280                 285

Thr Asn Gln Trp Val Asn Ser Tyr Lys Arg Ile Val Tyr Gly Asn Glu
290                 295                 300

Ala Pro Thr Ala Ala Thr Trp Gly Val Ser Asn Arg Ser Ala Leu Val
305                 310                 315                 320

Arg Val Pro Thr Tyr Arg Leu Asn Lys Glu Glu Ser Arg Arg Val Glu
            325                 330                 335

Val Arg Leu Pro Asp Thr Ala Cys Asn Pro Tyr Leu Ala Phe Ser Val
        340                 345                 350

Met Leu Gly Ala Gly Leu Lys Gly Ile Lys Glu Gly Tyr Glu Leu Asp
    355                 360                 365

Glu Pro Ala Glu Asp Ile Ser Asn Leu Ser Phe Arg Glu Arg Arg
370                 375                 380

Ala Met Gly Tyr Asn Asp Leu Pro Ser Ser Leu Asp Gln Ala Leu Arg
385                 390                 395                 400

Gln Met Glu Lys Ser Glu Leu Val Ala Asp Ile Leu Gly Glu His Val
            405                 410                 415

Phe Glu Phe Phe Leu Arg Asn Lys Trp Arg Glu Trp Arg Asp Tyr Gln
        420                 425                 430

Glu Gln Ile Thr Pro Trp Glu Leu Arg Asn Asn Leu Asp Tyr
    435                 440                 445

<210> SEQ ID NO 2
<211> LENGTH: 1341
<212> TYPE: DNA
<213> ORGANISM: Corynebacterium glutamicum ATCC13032

<400> SEQUENCE: 2 atg aac agc gaa cag gaa ttt gta ctc agc gcc att gaa gaa cgc gac    48
Met Asn Ser Glu Gln Glu Phe Val Leu Ser Ala Ile Glu Glu Arg Asp
 1               5                  10                  15 att aag ttt gtg cgt cta tgg ttc act gac att ctt ggc cac ttg aag    96
Ile Lys Phe Val Arg Leu Trp Phe Thr Asp Ile Leu Gly His Leu Lys
            20                  25                  30 tca gtg gtt gtg gct cct gca gaa cta gag tct gcg ttg gaa gaa ggc   144
Ser Val Val Val Ala Pro Ala Glu Leu Glu Ser Ala Leu Glu Glu Gly
        35                  40                  45 atc gga ttc gat ggc tca gcc att gag ggc tac gcg cgt atc tcg gaa   192
Ile Gly Phe Asp Gly Ser Ala Ile Glu Gly Tyr Ala Arg Ile Ser Glu
```

|  |  |
|---|---|
| gcg gac acc att gcc cgc cca gat cca tcg aca ttc cag gtc ctc cca<br>Ala Asp Thr Ile Ala Arg Pro Asp Pro Ser Thr Phe Gln Val Leu Pro<br>65                    70                  75                80 | 240 |
| cta gaa gcg ggc atc tca aaa ctg cag gca gca cgc ctg ttt tgc gat<br>Leu Glu Ala Gly Ile Ser Lys Leu Gln Ala Ala Arg Leu Phe Cys Asp<br>               85                  90                  95 | 288 |
| gtc acg atg cca gac gga cag cca tct ttt tct gac ccg cgc caa gtg<br>Val Thr Met Pro Asp Gly Gln Pro Ser Phe Ser Asp Pro Arg Gln Val<br>            100                  105                110 | 336 |
| ctg cgc agg cag gtc caa cta gct gca gat gaa ggc ttg acc tgc atg<br>Leu Arg Arg Gln Val Gln Leu Ala Ala Asp Glu Gly Leu Thr Cys Met<br>115                    120                  125 | 384 |
| atc tca cca gag att gag ttc tat ttg gtg caa agc ctt cgc acc aac<br>Ile Ser Pro Glu Ile Glu Phe Tyr Leu Val Gln Ser Leu Arg Thr Asn<br>130                    135                  140 | 432 |
| gga ctg cca cct gtg ccc act gac aac gga gga tat ttc gac caa gcc<br>Gly Leu Pro Pro Val Pro Thr Asp Asn Gly Gly Tyr Phe Asp Gln Ala<br>145                    150                  155                160 | 480 |
| aca ttc aat gag gcg ccg aat ttc cgt cga aac gcg atg gta gcg ctg<br>Thr Phe Asn Glu Ala Pro Asn Phe Arg Arg Asn Ala Met Val Ala Leu<br>               165                  170                175 | 528 |
| gag gaa ctc ggc atc cct gtc gag ttc tcc cac cat gaa act gca cct<br>Glu Glu Leu Gly Ile Pro Val Glu Phe Ser His His Glu Thr Ala Pro<br>            180                  185                190 | 576 |
| ggc cag caa gaa atc gat tta cgc cat gcg gat gcg ctc acc atg gcc<br>Gly Gln Gln Glu Ile Asp Leu Arg His Ala Asp Ala Leu Thr Met Ala<br>195                    200                  205 | 624 |
| gac aac atc atg acc ttc cgc tac atc atg aaa cag gtg gca agg gac<br>Asp Asn Ile Met Thr Phe Arg Tyr Ile Met Lys Gln Val Ala Arg Asp<br>210                    215                  220 | 672 |
| caa ggc gtc ggg gca tca ttt atg ccc aag cca ttc caa gaa cat gca<br>Gln Gly Val Gly Ala Ser Phe Met Pro Lys Pro Phe Gln Glu His Ala<br>225                    230                  235                240 | 720 |
| ggc tcc gcc atg cac acg cac atg tcc tta ttt gag ggc gat acc aac<br>Gly Ser Ala Met His Thr His Met Ser Leu Phe Glu Gly Asp Thr Asn<br>               245                  250                255 | 768 |
| gcg ttc cac gat cca gac gat tct tac atg ctg tcc aaa acc gca aaa<br>Ala Phe His Asp Pro Asp Asp Ser Tyr Met Leu Ser Lys Thr Ala Lys<br>            260                  265                270 | 816 |
| cag ttc atc gct gga atc ttg cat cac gct cca gaa ttc acc gct gtg<br>Gln Phe Ile Ala Gly Ile Leu His His Ala Pro Glu Phe Thr Ala Val<br>275                    280                  285 | 864 |
| acc aac cag tgg gtc aat tcc tac aaa cgc atc gtg tac gga aac gaa<br>Thr Asn Gln Trp Val Asn Ser Tyr Lys Arg Ile Val Tyr Gly Asn Glu<br>290                    295                  300 | 912 |
| gct cca act gcg gca acc tgg ggt gta tct aat cgt tct gcg ctg gtt<br>Ala Pro Thr Ala Ala Thr Trp Gly Val Ser Asn Arg Ser Ala Leu Val<br>305                    310                  315                320 | 960 |
| cgt gtt cct acc tac cgt ttg aat aag gag gag tcg cgc cgg gtg gag<br>Arg Val Pro Thr Tyr Arg Leu Asn Lys Glu Glu Ser Arg Arg Val Glu<br>               325                  330                335 | 1008 |
| gtg cgt ctt cct gat acc gct tgt aac cca tat ttg gcg ttt tca gtg<br>Val Arg Leu Pro Asp Thr Ala Cys Asn Pro Tyr Leu Ala Phe Ser Val<br>            340                  345                350 | 1056 |
| atg ctc ggc gct ggt ttg aaa ggc att aaa gaa ggt tat gag ctc gac<br>Met Leu Gly Ala Gly Leu Lys Gly Ile Lys Glu Gly Tyr Glu Leu Asp<br>355                    360                  365 | 1104 |
| gag cca gct gag gac gat atc tcc aac ttg agc ttc cgg gaa cgt cgc<br>Glu Pro Ala Glu Asp Asp Ile Ser Asn Leu Ser Phe Arg Glu Arg Arg | 1152 |

```
                370              375               380
gcc atg ggc tac aac gat ctg cca agc agc ctt gat cag gca ctg cgc      1200
Ala Met Gly Tyr Asn Asp Leu Pro Ser Ser Leu Asp Gln Ala Leu Arg
385                 390                 395                 400 caa atg gaa aag tca gag ctt gtt gct gac atc ctc ggt gag cac gtt      1248
Gln Met Glu Lys Ser Glu Leu Val Ala Asp Ile Leu Gly Glu His Val
                405                 410                 415 ttt gag ttt ttc ttg cgc aat aag tgg cgt gaa tgg cgt gac tac caa      1296
Phe Glu Phe Phe Leu Arg Asn Lys Trp Arg Glu Trp Arg Asp Tyr Gln
                420                 425                 430 gag cag atc act ccg tgg gag ctc cga aac aat ctt gat tac tag          1341
Glu Gln Ile Thr Pro Trp Glu Leu Arg Asn Asn Leu Asp Tyr ***
                435                 440                 445

<210> SEQ ID NO 3
<211> LENGTH: 1844
<212> TYPE: DNA
<213> ORGANISM: Corynebacterium glutamicum ATCC13032
<220> FEATURE:
<221> NAME/KEY: CDS
<222> LOCATION: (501)..(1838)

<400> SEQUENCE: 3
tacttagctt cggtagctcg gtgagaatct tctccagggt catcaccggc aagtggctag       60
tttcggcggc acgcgttccg ttcacccaca gtgtgtacat ctcatcggag caggagtaag      120
caatctcagg tagcgcgtga acaggagtg gatcaatatc ggcggaaaac tcatggcgga      180
gatcggcgga agtccaccca cgaagcgcac agaaacctag gtggctgatg atgctttctt      240
ctaaaatctg acggtaagag tcttgtgcgt cggtgacgtt gtcggagaag tgggagagag      300
tcattgcggt tccttattc gtaggagtgt tctaatttcg gtgcggttct cagtgaacca      360
cccaagctgg acacctccca ccccgtgtc atcaaaaaac gcgacatcc ttgagtaact      420 ctgagaaaaa ctaccccga tgggagtata aaagtggcaa atgcgcagtc gatgtcccat      480
cgctgcgtag attagttttc atg aac agc gaa cag gaa ttt gta ctc agc         530
                       Met Asn Ser Glu Gln Glu Phe Val Leu Ser
                         1               5                  10 gcc att gaa gaa cgc gac att aag ttt gtg cgt cta tgg ttc act gac       578
Ala Ile Glu Glu Arg Asp Ile Lys Phe Val Arg Leu Trp Phe Thr Asp
            15                  20                  25 att ctt ggc cac ttg aag tca gtg gtt gtg gct cct gca gaa cta gag       626
Ile Leu Gly His Leu Lys Ser Val Val Val Ala Pro Ala Glu Leu Glu
        30                  35                  40 tct gcg ttg gaa gaa ggc atc gga ttc gat ggc tca gcc att gag ggc       674
Ser Ala Leu Glu Glu Gly Ile Gly Phe Asp Gly Ser Ala Ile Glu Gly
    45                  50                  55 tac gcg cgt atc tcg gaa gcg gac acc att gcc cgc cca gat cca tcg       722
Tyr Ala Arg Ile Ser Glu Ala Asp Thr Ile Ala Arg Pro Asp Pro Ser
60                  65                  70 aca ttc cag gtc ctc cca cta gaa gcg ggc atc tca aaa ctg cag gca       770
Thr Phe Gln Val Leu Pro Leu Glu Ala Gly Ile Ser Lys Leu Gln Ala
75                  80                  85                  90 gca cgc ctg ttt tgc gat gtc acg atg cca gac gga cag cca tct ttt       818
Ala Arg Leu Phe Cys Asp Val Thr Met Pro Asp Gly Gln Pro Ser Phe
                95                 100                 105 tct gac ccg cgc caa gtg ctg cgc agg cag gtc caa cta gct gca gat       866
Ser Asp Pro Arg Gln Val Leu Arg Arg Gln Val Gln Leu Ala Ala Asp
            110                 115                 120 gaa ggc ttg acc tgc atg atc tca cca gag att gag ttc tat ttg gtg       914
Glu Gly Leu Thr Cys Met Ile Ser Pro Glu Ile Glu Phe Tyr Leu Val
        125                 130                 135
```

```
caa agc ctt cgc acc aac gga ctg cca cct gtg ccc act gac aac ggc     962
Gln Ser Leu Arg Thr Asn Gly Leu Pro Pro Val Pro Thr Asp Asn Gly
    140             145             150 gga tat ttc gac caa gcc aca ttc aat gag gcg ccg aat ttc cgt cga    1010
Gly Tyr Phe Asp Gln Ala Thr Phe Asn Glu Ala Pro Asn Phe Arg Arg
155             160             165             170 aac gcg atg gta gcg ctg gag gaa ctc ggc atc cct gtc gag ttc tcc    1058
Asn Ala Met Val Ala Leu Glu Glu Leu Gly Ile Pro Val Glu Phe Ser
                175             180             185 cac cat gaa act gca cct ggc cag caa gaa atc gat tta cgc cat gcg    1106
His His Glu Thr Ala Pro Gly Gln Gln Glu Ile Asp Leu Arg His Ala
            190             195             200 gat gcg ctc acc atg gcc gac aac atc atg acc ttc cgc tac atc atg    1154
Asp Ala Leu Thr Met Ala Asp Asn Ile Met Thr Phe Arg Tyr Ile Met
        205             210             215 aaa cag gtg gca agg gac caa ggc gtc ggg gca tca ttt atg ccc aag    1202
Lys Gln Val Ala Arg Asp Gln Gly Val Gly Ala Ser Phe Met Pro Lys
    220             225             230 cca ttc caa gaa cat gca ggc tcc gcc atg cac acg cac atg tcc tta    1250
Pro Phe Gln Glu His Ala Gly Ser Ala Met His Thr His Met Ser Leu
235             240             245             250 ttt gag ggc gat acc aac gcg ttc cac gat cca gac gat tct tac atg    1298
Phe Glu Gly Asp Thr Asn Ala Phe His Asp Pro Asp Asp Ser Tyr Met
                255             260             265 ctg tcc aaa acc gca aaa cag ttc atc gct gga atc ttg cat cac gct    1346
Leu Ser Lys Thr Ala Lys Gln Phe Ile Ala Gly Ile Leu His His Ala
            270             275             280 cca gaa ttc acc gct gtg acc aac cag tgg gtc aat tcc tac aaa cgc    1394
Pro Glu Phe Thr Ala Val Thr Asn Gln Trp Val Asn Ser Tyr Lys Arg
        285             290             295 atc gtg tac gga aac gaa gct cca act gcg gca acc tgg ggt gta tct    1442
Ile Val Tyr Gly Asn Glu Ala Pro Thr Ala Ala Thr Trp Gly Val Ser
    300             305             310 aat cgt tct gcg ctg gtt cgt gtt cct acc tac cgt ttg aat aag gag    1490
Asn Arg Ser Ala Leu Val Arg Val Pro Thr Tyr Arg Leu Asn Lys Glu
315             320             325             330 gag tcg cgc cgg gtg gag gtg cgt ctt cct gat acc gct tgt aac cca    1538
Glu Ser Arg Arg Val Glu Val Arg Leu Pro Asp Thr Ala Cys Asn Pro
                335             340             345 tat ttg gcg ttt tca gtg atg ctc ggc gct ggt ttg aaa ggc att aaa    1586
Tyr Leu Ala Phe Ser Val Met Leu Gly Ala Gly Leu Lys Gly Ile Lys
            350             355             360 gaa ggt tat gag ctc gac gag cca gct gag gac gat atc tcc aac ttg    1634
Glu Gly Tyr Glu Leu Asp Glu Pro Ala Glu Asp Asp Ile Ser Asn Leu
        365             370             375 agc ttc cgg gaa cgt cgc gcc atg ggc tac aac gat ctg cca agc agc    1682
Ser Phe Arg Glu Arg Arg Ala Met Gly Tyr Asn Asp Leu Pro Ser Ser
    380             385             390 ctt gat cag gca ctg cgc caa atg gaa aag tca gag ctt gtt gct gac    1730
Leu Asp Gln Ala Leu Arg Gln Met Glu Lys Ser Glu Leu Val Ala Asp
395             400             405             410 atc ctc ggt gag cac gtt ttt gag ttt ttc ttg cgc aat aag tgg cgt    1778
Ile Leu Gly Glu His Val Phe Glu Phe Phe Leu Arg Asn Lys Trp Arg
                415             420             425 gaa tgg cgt gac tac caa gag cag atc act ccg tgg gag ctc cga aac    1826
Glu Trp Arg Asp Tyr Gln Glu Gln Ile Thr Pro Trp Glu Leu Arg Asn
            430             435             440 aat ctt gat tac tagact                                             1844
Asn Leu Asp Tyr
445
```

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
tttggatcca aactcatggc ggagatcgg                                    29

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gcgtatctcg aaagcggaca c                                            21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
gtgtccgctt tcgagatacg c                                            21

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tttggatccg gcttgggcat aaatgatgc                                    29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
tttggatcct acttagcttc ggtagctcg                                    29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
tttggatcca gtctagtaat caagattgt                                    29

<210> SEQ ID NO 10
<211> LENGTH: 640
<212> TYPE: PRT
<213> ORGANISM: Corynebacterium glutamicum ATCC13032

<400> SEQUENCE: 10

Met Cys Gly Leu Leu Gly Ile Leu Thr Ala Asn Gly Asn Ala Glu Ala
 1               5                  10                  15

Phe Val Pro Ala Leu Glu Arg Ala Leu Pro Cys Met Arg His Arg Gly
            20                  25                  30

Pro Asp Asp Ala Gly Thr Trp His Asp Ala Asp Ala Phe Gly Phe
        35                  40                  45

Asn Arg Leu Ser Ile Ile Asp Ile Ala His Ser His Gln Pro Leu Arg
    50                  55                  60

Trp Gly Pro Ala Asp Glu Pro Asp Arg Tyr Ala Met Thr Phe Asn Gly
65                  70                  75                  80

Glu Ile Tyr Asn Tyr Val Glu Leu Arg Lys Glu Leu Ser Asp Leu Gly
                85                  90                  95

Tyr Ala Phe Asn Thr Ser Gly Asp Gly Glu Pro Ile Val Val Gly Phe
            100                 105                 110

His His Trp Gly Glu Ser Val Val Glu His Leu Arg Gly Met Phe Gly
        115                 120                 125

Ile Ala Ile Trp Asp Thr Lys Glu Lys Ser Leu Phe Leu Ala Arg Asp
130                 135                 140

Gln Phe Gly Ile Lys Pro Leu Phe Tyr Ala Thr Thr Glu His Gly Thr
145                 150                 155                 160

Val Phe Ser Ser Glu Lys Lys Thr Ile Leu Glu Met Ala Glu Glu Met
                165                 170                 175

Asn Leu Asp Leu Gly Leu Asp Lys Arg Thr Ile Glu His Tyr Val Asp
            180                 185                 190

Leu Gln Tyr Val Pro Glu Pro Asp Thr Leu His Ala Gln Ile Ser Arg
        195                 200                 205

Leu Glu Ser Gly Cys Thr Ala Thr Val Arg Pro Gly Gly Lys Leu Glu
    210                 215                 220

Gln Lys Arg Tyr Phe Lys Pro Gln Phe Pro Val Gln Lys Val Val Lys
225                 230                 235                 240

Gly Lys Glu Gln Asp Leu Phe Asp Arg Ile Ala Gln Val Leu Glu Asp
                245                 250                 255

Ser Val Glu Lys His Met Arg Ala Asp Val Thr Val Gly Ser Phe Leu
            260                 265                 270

Ser Gly Gly Ile Asp Ser Thr Ala Ile Ala Ala Leu Ala Lys Arg His
        275                 280                 285

Asn Pro Asp Leu Leu Thr Phe Thr Thr Gly Phe Glu Arg Glu Gly Tyr
    290                 295                 300

Ser Glu Val Asp Val Ala Ala Glu Ser Ala Ala Ile Gly Ala Glu
305                 310                 315                 320

His Ile Val Lys Ile Val Ser Pro Glu Glu Tyr Ala Asn Ala Ile Pro
                325                 330                 335

Lys Ile Met Trp Tyr Leu Asp Asp Pro Val Ala Asp Pro Ser Leu Val
            340                 345                 350

Pro Leu Tyr Phe Val Ala Glu Ala Arg Lys His Val Lys Val Val
        355                 360                 365

Leu Ser Gly Glu Gly Ala Asp Glu Leu Phe Gly Gly Tyr Thr Ile Tyr
    370                 375                 380

Lys Glu Pro Leu Ser Leu Ala Pro Phe Glu Lys Ile Pro Ser Pro Leu

```
                385                 390                 395                 400
Arg Lys Gly Leu Gly Lys Leu Ser Lys Val Leu Pro Asp Gly Met Lys
                405                 410                 415

Gly Lys Ser Leu Leu Glu Arg Gly Ser Met Thr Met Glu Glu Arg Tyr
            420                 425                 430

Tyr Gly Asn Ala Arg Ser Phe Asn Phe Glu Gln Met Gln Arg Val Ile
        435                 440                 445

Pro Trp Ala Lys Arg Glu Trp Asp His Arg Glu Val Thr Ala Pro Ile
    450                 455                 460

Tyr Ala Gln Ser Arg Asn Phe Asp Pro Val Ala Arg Met Gln His Leu
465                 470                 475                 480

Asp Leu Phe Thr Trp Met Arg Gly Asp Ile Leu Val Lys Ala Asp Lys
                485                 490                 495

Ile Asn Met Ala Asn Ser Leu Glu Leu Arg Val Pro Phe Leu Asp Lys
            500                 505                 510

Glu Val Phe Lys Val Ala Glu Thr Ile Pro Tyr Asp Leu Lys Ile Ala
        515                 520                 525

Asn Gly Thr Thr Lys Tyr Ala Leu Arg Arg Ala Leu Glu Gln Ile Val
    530                 535                 540

Pro Pro His Val Leu His Arg Lys Lys Leu Gly Phe Pro Val Pro Met
545                 550                 555                 560

Arg His Trp Leu Ala Gly Asp Glu Leu Phe Gly Trp Ala Gln Asp Thr
                565                 570                 575

Ile Lys Glu Ser Gly Thr Glu Asp Ile Phe Asn Lys Gln Ala Val Leu
            580                 585                 590

Asp Met Leu Asn Glu His Arg Asp Gly Val Ser Asp His Ser Arg Arg
        595                 600                 605

Leu Trp Thr Val Leu Ser Phe Met Val Trp His Gly Ile Phe Val Glu
    610                 615                 620

Asn Arg Ile Asp Pro Gln Ile Glu Asp Arg Ser Tyr Pro Val Glu Leu
625                 630                 635                 640

<210> SEQ ID NO 11
<211> LENGTH: 1923
<212> TYPE: DNA
<213> ORGANISM: Corynebacterium glutamicum ATCC13032

<400> SEQUENCE: 11 atg tgc ggc ctt ctt ggc ata ttg act gca aat ggg aac gct gaa gca      48
Met Cys Gly Leu Leu Gly Ile Leu Thr Ala Asn Gly Asn Ala Glu Ala
 1               5                  10                  15 ttc gtt cct gca ctc gag cgg gcc ttg cca tgc atg cgc cac cgt ggt      96
Phe Val Pro Ala Leu Glu Arg Ala Leu Pro Cys Met Arg His Arg Gly
            20                  25                  30 cct gac gat gcc ggc act tgg cat gac gcc gat gca gcg ttt gga ttc     144
Pro Asp Asp Ala Gly Thr Trp His Asp Ala Asp Ala Ala Phe Gly Phe
        35                  40                  45 aac cgc ctc tcc atc att gat att gca cac tcc cac caa cca ctg cgt     192
Asn Arg Leu Ser Ile Ile Asp Ile Ala His Ser His Gln Pro Leu Arg
    50                  55                  60 tgg gga cct gcg gat gaa ccc gac cgc tac gca atg act ttc aac ggt     240
Trp Gly Pro Ala Asp Glu Pro Asp Arg Tyr Ala Met Thr Phe Asn Gly
65                  70                  75                  80 gag atc tac aac tac gtt gag ctg cgt aaa gag ctc tcg gat ttg gga     288
Glu Ile Tyr Asn Tyr Val Glu Leu Arg Lys Glu Leu Ser Asp Leu Gly
                85                  90                  95 tat gcc ttt aat act tct ggc gat ggc gag cca att gtt gtc ggt ttc     336
Tyr Ala Phe Asn Thr Ser Gly Asp Gly Glu Pro Ile Val Val Gly Phe
```

```
        Tyr Ala Phe Asn Thr Ser Gly Asp Gly Glu Pro Ile Val Val Gly Phe
                        100                 105                 110 cac cac tgg ggc gag tcc gtg gtc gag cat ctc cgc gga atg ttc ggc        384
His His Trp Gly Glu Ser Val Val Glu His Leu Arg Gly Met Phe Gly
            115                 120                 125 att gcc att tgg gat aca aag gaa aag tcg ctt ttc ctt gcg cgt gat        432
Ile Ala Ile Trp Asp Thr Lys Glu Lys Ser Leu Phe Leu Ala Arg Asp
130                 135                 140 cag ttc ggc att aag cca ctg ttc tac gca acc acc gag cat ggc acc        480
Gln Phe Gly Ile Lys Pro Leu Phe Tyr Ala Thr Thr Glu His Gly Thr
145                 150                 155                 160 gtg ttc tcc tca gag aag aag acc atc ttg gag atg gcc gag gag atg        528
Val Phe Ser Ser Glu Lys Lys Thr Ile Leu Glu Met Ala Glu Glu Met
                165                 170                 175 aat cta gat ctg ggc ctt gat aag cgc acc att gag cac tac gtg gac        576
Asn Leu Asp Leu Gly Leu Asp Lys Arg Thr Ile Glu His Tyr Val Asp
            180                 185                 190 ttg cag tac gtg ccc gag cca gat acc ctt cac gcg cag att tcc cgc        624
Leu Gln Tyr Val Pro Glu Pro Asp Thr Leu His Ala Gln Ile Ser Arg
        195                 200                 205 ttg gag tca ggc tgc acc gca aca gtt cgt ccg ggc ggc aag ctg gaa        672
Leu Glu Ser Gly Cys Thr Ala Thr Val Arg Pro Gly Gly Lys Leu Glu
210                 215                 220 cag aag cgt tac ttc aag cct cag ttc cca gta cag aag gtc gta aag        720
Gln Lys Arg Tyr Phe Lys Pro Gln Phe Pro Val Gln Lys Val Val Lys
225                 230                 235                 240 ggt aag gag cag gac ctc ttc gat cgc att gcc cag gtg ttg gag gat        768
Gly Lys Glu Gln Asp Leu Phe Asp Arg Ile Ala Gln Val Leu Glu Asp
                245                 250                 255 agc gtc gaa aag cat atg cgt gcc gac gtg acc gta ggc tcg ttc ctt        816
Ser Val Glu Lys His Met Arg Ala Asp Val Thr Val Gly Ser Phe Leu
            260                 265                 270 tcc ggc ggc att gac tca acc gca att gcg gcg ctt gca aag cgc cac        864
Ser Gly Gly Ile Asp Ser Thr Ala Ile Ala Ala Leu Ala Lys Arg His
        275                 280                 285 aac cct gac ctg ctc acc ttc acc acc ggt ttc gag cgt gaa ggc tac        912
Asn Pro Asp Leu Leu Thr Phe Thr Thr Gly Phe Glu Arg Glu Gly Tyr
290                 295                 300 tcg gag gtc gat gtg gct gcg gag tcc gcc gct gcg att ggc gct gag        960
Ser Glu Val Asp Val Ala Ala Glu Ser Ala Ala Ala Ile Gly Ala Glu
305                 310                 315                 320 cac atc gtg aag att gtc tcg cct gag gaa tac gcc aac gcg att cct        1008
His Ile Val Lys Ile Val Ser Pro Glu Glu Tyr Ala Asn Ala Ile Pro
                325                 330                 335 aag atc atg tgg tac ttg gat gat cct gta gct gac cca tca ttg gtc        1056
Lys Ile Met Trp Tyr Leu Asp Asp Pro Val Ala Asp Pro Ser Leu Val
            340                 345                 350 ccg ctg tac ttc gtg gca gcg gaa gca cgt aag cac gtc aag gtt gtg        1104
Pro Leu Tyr Phe Val Ala Ala Glu Ala Arg Lys His Val Lys Val Val
        355                 360                 365 ctg tct ggc gag ggc gca gat gag ctg ttc ggt gga tac acc att tac        1152
Leu Ser Gly Glu Gly Ala Asp Glu Leu Phe Gly Gly Tyr Thr Ile Tyr
370                 375                 380 aag gag ccg cta tcg ctt gct cca ttt gag aag atc cct tcc cca cta        1200
Lys Glu Pro Leu Ser Leu Ala Pro Phe Glu Lys Ile Pro Ser Pro Leu
385                 390                 395                 400 cgt aaa ggc ctg gga aag ctc agc aag gtt ctg cca gac ggc atg aag        1248
Arg Lys Gly Leu Gly Lys Leu Ser Lys Val Leu Pro Asp Gly Met Lys
                405                 410                 415 ggc aag tcc ctt ctt gag cgt ggc tcc atg acc atg gaa gag cgc tac        1296
```

```
                Gly Lys Ser Leu Leu Glu Arg Gly Ser Met Thr Met Glu Glu Arg Tyr
                              420                 425                 430 tac ggc aac gct cgc tcc ttc aat ttc gag cag atg caa cgc gtt att          1344
Tyr Gly Asn Ala Arg Ser Phe Asn Phe Glu Gln Met Gln Arg Val Ile
            435                 440                 445 cca tgg gca aag cgc gaa tgg gac cac cgc gaa gtc act gcg ccg atc          1392
Pro Trp Ala Lys Arg Glu Trp Asp His Arg Glu Val Thr Ala Pro Ile
    450                 455                 460 tac gca cag tcc cgc aac ttt gat cca gta gcc cgc atg caa cac ctg          1440
Tyr Ala Gln Ser Arg Asn Phe Asp Pro Val Ala Arg Met Gln His Leu
465                 470                 475                 480 gat ctg ttc acc tgg atg cgc ggc gac atc ctg gtc aag gct gac aag          1488
Asp Leu Phe Thr Trp Met Arg Gly Asp Ile Leu Val Lys Ala Asp Lys
                485                 490                 495 atc aac atg gcg aac tcc ctt gag ctg cga gtt cca ttc ttg gat aag          1536
Ile Asn Met Ala Asn Ser Leu Glu Leu Arg Val Pro Phe Leu Asp Lys
            500                 505                 510 gaa gtt ttc aag gtt gca gag acc att cct tac gac ctg aag att gcc          1584
Glu Val Phe Lys Val Ala Glu Thr Ile Pro Tyr Asp Leu Lys Ile Ala
        515                 520                 525 aac ggt acc acc aag tac gcg ctg cgc agg gca ctc gag cag att gtt          1632
Asn Gly Thr Thr Lys Tyr Ala Leu Arg Arg Ala Leu Glu Gln Ile Val
    530                 535                 540 ccg cct cac gtt ttg cac cgc aag aag ctg ggc ttc cct gtt ccc atg          1680
Pro Pro His Val Leu His Arg Lys Lys Leu Gly Phe Pro Val Pro Met
545                 550                 555                 560 cgc cac tgg ctt gcc ggc gat gag ctg ttc ggt tgg gcg cag gac acc          1728
Arg His Trp Leu Ala Gly Asp Glu Leu Phe Gly Trp Ala Gln Asp Thr
                565                 570                 575 atc aag gaa tcc ggt act gaa gat atc ttc aac aag cag gct gtg ctg          1776
Ile Lys Glu Ser Gly Thr Glu Asp Ile Phe Asn Lys Gln Ala Val Leu
            580                 585                 590 gat atg ctg aac gag cac cgc gat ggc gtg tca gat cat tcc cgt cga          1824
Asp Met Leu Asn Glu His Arg Asp Gly Val Ser Asp His Ser Arg Arg
        595                 600                 605 ctg tgg act gtt ctg tca ttt atg gtg tgg cac ggc att ttt gtg gaa          1872
Leu Trp Thr Val Leu Ser Phe Met Val Trp His Gly Ile Phe Val Glu
    610                 615                 620 aac cgc att gat cca cag att gag gac cgc tcc tac cca gtc gag ctt          1920
Asn Arg Ile Asp Pro Gln Ile Glu Asp Arg Ser Tyr Pro Val Glu Leu
625                 630                 635                 640 taa                                                                       1923
***

<210> SEQ ID NO 12
<211> LENGTH: 2188
<212> TYPE: DNA
<213> ORGANISM: Corynebacterium glutamicum ATCC13032
<220> FEATURE:
<221> NAME/KEY: CDS
<222> LOCATION: (263)..(2182)

<400> SEQUENCE: 12 cccacccctta cccctacgt tcctacaagg tgcatgtatt aggaaatcaa tctggttttc          60
aggaaccttt gagaatgctg caatagtcag ctgacgcacg ttgcttgagg gagctttcgt         120
caattttggc gtgccctttt cacctcagat gtaacttcgc cgtatcgttg acacgagatt         180
taacaaatgc agcgtcttat ttcttccaac aaaatttctt tgcgatttaa ggcgcctttt         240
atttcaggag gattttttcaa tc atg tgc ggc ctt ctt ggc ata ttg act gca         292
                          Met Cys Gly Leu Leu Gly Ile Leu Thr Ala
                           1               5                  10
```

| | | |
|---|---|---|
| aat ggg aac gct gaa gca ttc gtt cct gca ctc gag cgg gcc ttg cca<br>Asn Gly Asn Ala Glu Ala Phe Val Pro Ala Leu Glu Arg Ala Leu Pro<br>             15                     20                  25 | 340 |
| tgc atg cgc cac cgt ggt cct gac gat gcc ggc act tgg cat gac gcc<br>Cys Met Arg His Arg Gly Pro Asp Asp Ala Gly Thr Trp His Asp Ala<br>             30                     35                  40 | 388 |
| gat gca gcg ttt gga ttc aac cgc ctc tcc atc att gat att gca cac<br>Asp Ala Ala Phe Gly Phe Asn Arg Leu Ser Ile Ile Asp Ile Ala His<br>                45                    50                  55 | 436 |
| tcc cac caa cca ctg cgt tgg gga cct gcg gat gaa ccc gac cgc tac<br>Ser His Gln Pro Leu Arg Trp Gly Pro Ala Asp Glu Pro Asp Arg Tyr<br>    60                     65                     70 | 484 |
| gca atg act ttc aac ggt gag atc tac aac tac gtt gag ctg cgt aaa<br>Ala Met Thr Phe Asn Gly Glu Ile Tyr Asn Tyr Val Glu Leu Arg Lys<br>75                     80                     85                  90 | 532 |
| gag ctc tcg gat ttg gga tat gcc ttt aat act tct ggc gat ggc gag<br>Glu Leu Ser Asp Leu Gly Tyr Ala Phe Asn Thr Ser Gly Asp Gly Glu<br>                95                    100               105 | 580 |
| cca att gtt gtc ggt ttc cac cac tgg ggc gag tcc gtg gtc gag cat<br>Pro Ile Val Val Gly Phe His His Trp Gly Glu Ser Val Val Glu His<br>             110                  115             120 | 628 |
| ctc cgc gga atg ttc ggc att gcc att tgg gat aca aag gaa aag tcg<br>Leu Arg Gly Met Phe Gly Ile Ala Ile Trp Asp Thr Lys Glu Lys Ser<br>        125                 130                  135 | 676 |
| ctt ttc ctt gcg cgt gat cag ttc ggc att aag cca ctg ttc tac gca<br>Leu Phe Leu Ala Arg Asp Gln Phe Gly Ile Lys Pro Leu Phe Tyr Ala<br>140                     145                     150 | 724 |
| acc acc gag cat ggc acc gtg ttc tcc tca gag aag aag acc atc ttg<br>Thr Thr Glu His Gly Thr Val Phe Ser Ser Glu Lys Lys Thr Ile Leu<br>155                     160                     165               170 | 772 |
| gag atg gcc gag gag atg aat cta gat ctg ggc ctt gat aag cgc acc<br>Glu Met Ala Glu Glu Met Asn Leu Asp Leu Gly Leu Asp Lys Arg Thr<br>                   175                     180               185 | 820 |
| att gag cac tac gtg gac ttg cag tac gtg ccc gag cca gat acc ctt<br>Ile Glu His Tyr Val Asp Leu Gln Tyr Val Pro Glu Pro Asp Thr Leu<br>             190                  195             200 | 868 |
| cac gcg cag att tcc cgc ttg gag tca ggc tgc acc gca aca gtt cgt<br>His Ala Gln Ile Ser Arg Leu Glu Ser Gly Cys Thr Ala Thr Val Arg<br>        205                 210                  215 | 916 |
| ccg ggc ggc aag ctg gaa cag aag cgt tac ttc aag cct cag ttc cca<br>Pro Gly Gly Lys Leu Glu Gln Lys Arg Tyr Phe Lys Pro Gln Phe Pro<br>220                     225                     230 | 964 |
| gta cag aag gtc gta aag ggt aag gag cag gac ctc ttc gat cgc att<br>Val Gln Lys Val Val Lys Gly Lys Glu Gln Asp Leu Phe Asp Arg Ile<br>235                     240                     245               250 | 1012 |
| gcc cag gtg ttg gag gat agc gtc gaa aag cat atg cgt gcc gac gtg<br>Ala Gln Val Leu Glu Asp Ser Val Glu Lys His Met Arg Ala Asp Val<br>             255                  260             265 | 1060 |
| acc gta ggc tcg ttc ctt tcc ggc ggc att gac tca acc gca att gcg<br>Thr Val Gly Ser Phe Leu Ser Gly Gly Ile Asp Ser Thr Ala Ile Ala<br>                 270                 275             280 | 1108 |
| gcg ctt gca aag cgc cac aac cct gac ctg ctc acc ttc acc acc ggt<br>Ala Leu Ala Lys Arg His Asn Pro Asp Leu Leu Thr Phe Thr Thr Gly<br>        285                 290                  295 | 1156 |
| ttc gag cgt gaa ggc tac tcg gag gtc gat gtg gct gcg gag tcc gcc<br>Phe Glu Arg Glu Gly Tyr Ser Glu Val Asp Val Ala Ala Glu Ser Ala<br>300                     305                     310 | 1204 |
| gct gcg att ggc gct gag cac atc gtg aag att gtc tcg cct gag gaa<br>Ala Ala Ile Gly Ala Glu His Ile Val Lys Ile Val Ser Pro Glu Glu<br>315                     320                     325               330 | 1252 |

```
tac gcc aac gcg att cct aag atc atg tgg tac ttg gat gat cct gta    1300
Tyr Ala Asn Ala Ile Pro Lys Ile Met Trp Tyr Leu Asp Asp Pro Val
            335                 340                 345 gct gac cca tca ttg gtc ccg ctg tac ttc gtg gca gcg gaa gca cgt    1348
Ala Asp Pro Ser Leu Val Pro Leu Tyr Phe Val Ala Ala Glu Ala Arg
        350                 355                 360 aag cac gtc aag gtt gtg ctg tct ggc gag ggc gca gat gag ctg ttc    1396
Lys His Val Lys Val Val Leu Ser Gly Glu Gly Ala Asp Glu Leu Phe
    365                 370                 375 ggt gga tac acc att tac aag gag ccg cta tcg ctt gct cca ttt gag    1444
Gly Gly Tyr Thr Ile Tyr Lys Glu Pro Leu Ser Leu Ala Pro Phe Glu
380                 385                 390 aag atc cct tcc cca cta cgt aaa ggc ctg gga aag ctc agc aag gtt    1492
Lys Ile Pro Ser Pro Leu Arg Lys Gly Leu Gly Lys Leu Ser Lys Val
395                 400                 405                 410 ctg cca gac ggc atg aag ggc aag tcc ctt ctt gag cgt ggc tcc atg    1540
Leu Pro Asp Gly Met Lys Gly Lys Ser Leu Leu Glu Arg Gly Ser Met
                415                 420                 425 acc atg gaa gag cgc tac tac ggc aac gct cgc tcc ttc aat ttc gag    1588
Thr Met Glu Glu Arg Tyr Tyr Gly Asn Ala Arg Ser Phe Asn Phe Glu
            430                 435                 440 cag atg caa cgc gtt att cca tgg gca aag cgc gaa tgg gac cac cgc    1636
Gln Met Gln Arg Val Ile Pro Trp Ala Lys Arg Glu Trp Asp His Arg
        445                 450                 455 gaa gtc act gcg ccg atc tac gca cag tcc cgc aac ttt gat cca gta    1684
Glu Val Thr Ala Pro Ile Tyr Ala Gln Ser Arg Asn Phe Asp Pro Val
    460                 465                 470 gcc cgc atg caa cac ctg gat ctg ttc acc tgg atg cgc ggc gac atc    1732
Ala Arg Met Gln His Leu Asp Leu Phe Thr Trp Met Arg Gly Asp Ile
475                 480                 485                 490 ctg gtc aag gct gac aag atc aac atg gcg aac tcc ctt gag ctg cga    1780
Leu Val Lys Ala Asp Lys Ile Asn Met Ala Asn Ser Leu Glu Leu Arg
                495                 500                 505 gtt cca ttc ttg gat aag gaa gtt ttc aag gtt gca gag acc att cct    1828
Val Pro Phe Leu Asp Lys Glu Val Phe Lys Val Ala Glu Thr Ile Pro
            510                 515                 520 tac gac ctg aag att gcc aac ggt acc acc aag tac gcg ctg cgc agg    1876
Tyr Asp Leu Lys Ile Ala Asn Gly Thr Thr Lys Tyr Ala Leu Arg Arg
        525                 530                 535 gca ctc gag cag att gtt ccg cct cac gtt ttg cac cgc aag aag ctg    1924
Ala Leu Glu Gln Ile Val Pro Pro His Val Leu His Arg Lys Lys Leu
    540                 545                 550 ggc ttc cct gtt ccc atg cgc cac tgg ctt gcc ggc gat gag ctg ttc    1972
Gly Phe Pro Val Pro Met Arg His Trp Leu Ala Gly Asp Glu Leu Phe
555                 560                 565                 570 ggt tgg gcg cag gac acc atc aag gaa tcc ggt act gaa gat atc ttc    2020
Gly Trp Ala Gln Asp Thr Ile Lys Glu Ser Gly Thr Glu Asp Ile Phe
                575                 580                 585 aac aag cag gct gtg ctg gat atg ctg aac gag cac cgc gat ggc gtg    2068
Asn Lys Gln Ala Val Leu Asp Met Leu Asn Glu His Arg Asp Gly Val
            590                 595                 600 tca gat cat tcc cgt cga ctg tgg act gtt ctg tca ttt atg gtg tgg    2116
Ser Asp His Ser Arg Arg Leu Trp Thr Val Leu Ser Phe Met Val Trp
        605                 610                 615 cac ggc att ttt gtg gaa aac cgc att gat cca cag att gag gac cgc    2164
His Gly Ile Phe Val Glu Asn Arg Ile Asp Pro Gln Ile Glu Asp Arg
    620                 625                 630 tcc tac cca gtc gag ctt taagtc                                     2188
Ser Tyr Pro Val Glu Leu
635                 640
```

```
<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
tttggatccc ccaccettac ccctacgt                                       29

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gtagatctca tcgttgaaag t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
actttcaacg atgagatcta c                                              21

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
tttggatccg aggtcctgct ccttaccct                                      29
```

US 8,067,211 B2

METHOD FOR PRODUCTION OF L-GLUTAMINE

TECHNICAL FIELD

The present invention relates to a process for producing L-glutamine.

BACKGROUND ART

As a process for producing L-glutamine by fermentation, a method which involves a coryneform bacterium provided with azaserine resistance (cf. Patent Reference 1), a method which involves a coryneform bacterium provided with 6-diazo-5-oxo-norleucine resistance (cf. Patent Reference 2) and the like are known. In addition, as a process for producing L-glutamine by reinforcing glutamine synthetase activity, methods which involve a coryneform bacterium having reduced glutamine synthetase-adenylyl transferase activity which is controlled by adenylylation (cf. Non-patent reference 1, Patent Reference 3), and a coryneform bacterium in which an amino acid at position 405 of glutamine synthetase which is subjected to adenylylation is substituted and a coryneform bacterium having decreased activity of PII protein (cf. Non-patent Reference 2, Patent Reference 3) are known.

It is known that, in addition to glnA which encodes a glutamine synthetase, glnA2 which encodes a glutamine synthetase 2 having homology with glutamine synthetase is present on the genome of coryneform bacteria. It was reported that the polypeptide encoded by glnA2 of a coryneform bacterium has high homology with a glutamine synthetase of *Bacillus subtilis* which is not controlled by adenylylation, but the coryneform bacterium shows glutamine auxotrophic phenotype when glnA encoding a glutamine synthetase which is controlled by adenylylation is deactivated (cf. Non-patent Reference 1). In coryneform bacteria, the polypeptide encoded by glnA2 does not have glutamine synthetase activity, and there are no cases so far in which L-glutamine was produced by modification of glnA2.

In addition, it was reported that in *Corynebacterium glutamicum*, glutamic acid is produced by reduction of activity of a polypeptide which is encoded by ItsA and concerned in lysozyme sensitivity (cf. Non-patent Reference 3, Non-patent Reference 4, Patent Reference 4).

Patent Reference 1: Japanese Published Unexamined Patent Application No. 148094/80
Patent Reference 2: Japanese Published Unexamined Patent Application No. 232497/91
Patent Reference 3: Japanese Published Unexamined Patent Application No. 300887/02
Patent Reference 4: WO 00/14241
Non-patent Reference 1: *FEMS Microbiology Letters*, 201, 91 (2001)
Non-patent Reference 2: *FEMS Microbiology Letters*, 173, 303 (1999)
Non-patent Reference 3: *BMC Biotechnol.*, 1, 9 (2001)
Non-patent Reference 4: *Journal of Bacteriology*, 182, 2696 (2000)

DISCLOSURE OF THE INVENTION

Problems to be Solved by the Invention

An object of the present invention is to provide a modified glutamine synthetase 2, a DNA encoding the modified glutamine synthetase 2, a recombinant DNA comprising the DNA, a transformant carrying the recombinant DNA, a microorganism comprising the DNA on its chromosome, and a process for producing L-glutamine using the transformant or the microorganism.

Means for Solving the Problems

The present invention relates to the following (1) to (34).
(1) A polypeptide which comprises an amino acid sequence in which one or more amino acids are deleted, substituted or added in the amino acid sequence of a glutamine synthetase 2 derived from a microorganism belonging to a coryneform bacterium, wherein the polypeptide confers a larger production amount of L-glutamine on a wild type coryneform bacterium when the polypeptide is expressed in the wild type coryneform bacterium as a host cell, than that of the wild type coryneform bacterium.
(2) The polypeptide according to the above (1), which comprises an amino acid sequence in which, in the amino acid sequence of a glutamine synthetase 2, an amino acid at a position corresponding to the amino acid at position 64 from the N-terminal in the amino acid sequence of SEQ ID NO:1 is substituted with an amino acid other than glutamic acid.
(3) The polypeptide according to the above (1), which comprises an amino acid sequence in which, in the amino acid sequence of a glutamine synthetase 2, an amino acid at a position corresponding to the amino acid at position 64 from the N-terminal in the amino acid sequence of SEQ ID NO:1 is substituted with an amino acid other than glutamic acid, and further one or more amino acids are deleted, substituted or added.
(4) The polypeptide according to the above (2) or (3), wherein the amino acid other than glutamic acid is a basic amino acid.
(5) The polypeptide according to the above (2) or (3), wherein the amino acid other than glutamic acid is lysine.
(6) The polypeptide according to any one of the above (1) to (5), wherein the microorganism belonging to a coryneform bacterium is a microorganism belonging to the genus *Corynebacterium*, the genus *Brevibacterium* or the genus *Mycobacterium*.
(7) The polypeptide according to the above (1), wherein the amino acid sequence of a glutamine synthetase 2 is the amino acid sequence of SEQ ID NO:1.
(8) The polypeptide according to the above (7), which comprises an amino acid sequence in which the amino acid at position 64 from the N-terminal in the amino acid sequence of SEQ ID NO:1 is substituted with an amino acid other than glutamic acid.
(9) The polypeptide according to the above (7), which comprises an amino acid sequence in which glutamic acid at position 64 from the N-terminal in the amino acid sequence of SEQ ID NO:1 is substituted with an amino acid other than glutamic acid, and further one or more amino acids are deleted, substituted or added.
(10) The polypeptide according to the above (8) or (9), wherein the amino acid other than glutamic acid is a basic amino acid.
(11) The polypeptide according to the above (8) or (9), wherein the amino acid other than glutamic acid is lysine.
(12) A DNA encoding the polypeptide according to any one of the above (1) to (11).
(13) The DNA according to the above (12), which comprises a nucleotide sequence in which, in the nucleotide sequence of a DNA encoding the glutamine synthetase 2 derived from a microorganism belonging to a coryneform bacterium, a region corresponding to the nucleotide sequence at positions 190 to 192 from the 5'-terminal in the nucleotide sequence of SEQ ID NO:2 is a codon encoding an amino acid other than glutamic acid.

(14) The DNA according to the above (13), wherein the codon encoding an amino acid other than glutamic acid is a codon encoding a basic amino acid.

(15) The DNA according to the above (13), wherein the codon encoding an amino acid other than glutamic acid is a codon encoding lysine.

(16) The DNA according to any one of the above (13) to (15), wherein the microorganism belonging to a coryneform bacterium is a microorganism belonging to the genus *Corynebacterium*, the genus *Brevibacterium* or the genus *Mycobacterium*.

(17) The DNA according to the above (12), which comprises a nucleotide sequence in which the nucleotide sequence at positions 190 to 192 from the 5'-terminal in the nucleotide sequence of SEQ ID NO:2 is a codon encoding an amino acid other than glutamic acid.

(18) The DNA according to the above (17), wherein the codon encoding an amino acid other than glutamic acid is a codon encoding a basic amino acid.

(19) The DNA according to the above (17), wherein the codon encoding an amino acid other than glutamic acid is a codon encoding lysine.

(20) A DNA which hybridizes with a DNA consisting of a nucleotide sequence complementary to the nucleotide sequence of SEQ ID NO:2 under stringent conditions, and comprises a nucleotide sequence in which a region corresponding to the nucleotide sequence at positions 190 to 192 from the 5'-terminal in the nucleotide sequence of SEQ ID NO:2 is a codon encoding an amino acid other than glutamic acid, wherein a production amount of L-glutamine in a transformant obtained by introducing the DNA into a wild type coryneform bacterium is larger than that of the wild type coryneform bacterium.

(21) The DNA according to the above (20), wherein the codon encoding an amino acid other than glutamic acid is a codon encoding a basic amino acid.

(22) The DNA according to the above (20), wherein the codon encoding an amino acid other than glutamic acid is a codon encoding lysine.

(23) A recombinant DNA which comprises the DNA according to any one of the above (12) to (22).

(24) A microorganism transformed with the recombinant DNA according to the above (23).

(25) A microorganism which comprises, on its chromosomal DNA, the DNA according to any one of the above (12) to (22).

(26) The microorganism according to the above (24) or (25), which has ability of producing a polypeptide comprising an amino acid sequence in which one or more amino acids are deleted, substituted or added in the amino acid sequence of LtsA derived from a microorganism belonging to a coryneform bacterium, and has lysozyme sensitivity.

(27) The microorganism according to the above (26), wherein the polypeptide comprises an amino acid sequence in which an amino acid at a position corresponding to the amino acid at position 80 from the N-terminal in the amino acid sequence of SEQ ID NO:10 is an amino acid other than glycine.

(28) The microorganism according to the above (27), wherein the amino acid other than glycine is aspartic acid.

(29) The microorganism according to the above (26), wherein the amino acid sequence of LtsA is the amino acid sequence of SEQ ID NO:10.

(30) The microorganism according to the above (29), wherein the polypeptide comprises an amino acid sequence in which the amino acid at position 80 from the N-terminal in the amino acid sequence of SEQ ID NO:10 is an amino acid other than glycine.

(31) The microorganism according to the above (30), wherein the amino acid other than glycine is aspartic acid.

(32) The microorganism according to any one of the above (24) to (31), wherein the microorganism is a microorganism belonging to the genus *Corynebacterium*, the genus *Brevibacterium* or the genus *Mycobacterium*.

(33) The microorganism according to the above (32), wherein the microorganism belonging to the genus *Corynebacterium* is *Corynebacterium glutamicum*.

(34) A process for producing L-glutamine, which comprises culturing the microorganism according to any one of the above (24) to (33) in a medium to form and accumulating L-glutamine in a culture, and recovering L-glutamine from the culture.

Effect of the Invention

According to the present invention, a modified glutamine synthetase 2 and a DNA encoding the modified glutamine synthetase 2 are obtained, and L-glutamine can be produced by a microorganism comprising the DNA. In addition, L-glutamine can be further efficiently produced by introducing a mutation into the gene of the microorganism encoding LtsA.

BEST MODE FOR CARRYING OUT THE INVENTION

The present invention is described below in detail.
(1) Polypeptide of the Present Invention Examples of the polypeptide of the present invention include:

(i) a polypeptide which comprises an amino acid sequence in which one or more amino acids are deleted, substituted or added in the amino acid sequence of a glutamine synthetase 2 derived from a microorganism belonging to a coryneform bacterium, wherein the polypeptide confers a larger production amount of L-glutamine on a wild type coryneform bacterium when the polypeptide is expressed in the wild type coryneform bacterium as a host cell, than that of the wild type coryneform bacterium.

(ii) the polypeptide according to the above (i), which comprises an amino acid sequence in which, in the amino acid sequence of a glutamine synthetase 2, an amino acid at a position corresponding to the amino acid at position 64 from the N-terminal in the amino acid sequence of SEQ ID NO:1 is substituted with an amino acid other than glutamic acid, (iii) the polypeptide according to the above (i), which comprises an amino acid sequence in which, in the amino acid sequence of a glutamine synthetase 2, an amino acid at a position corresponding to the amino acid at position 64 from the N-terminal in the amino acid sequence of SEQ ID NO:1 is substituted with an amino acid other than glutamic acid, and further one or more amino acids are deleted, substituted or added, (iv) the polypeptide according to the above (ii) or (iii), wherein the amino acid other than glutamic acid is a basic amino acid, (v) the polypeptide according to the above (ii) or (iii), wherein the amino acid other than glutamic acid is lysine, (vi) the polypeptide according to any one of the above (i) to (v), wherein the microorganism belonging to a coryneform bacterium is a microorganism belonging to the genus *Corynebacterium*, the genus *Brevibacterium* or the genus *Mycobacterium*, (vii) the polypeptide according to the above (i), wherein the amino acid sequence of a glutamine synthetase 2 is the amino acid sequence of SEQ ID NO:1, (viii) the polypeptide according to the above (vii), which comprises an amino acid sequence in which the amino acid at position 64 from the N-terminal in the amino acid sequence of SEQ ID NO:1 is substituted with an amino acid other than glutamic acid, (ix) the polypeptide according to the above (vii), which comprises an amino acid sequence in which glutamic acid at position 64 from the N-terminal in the amino acid sequence of SEQ ID NO:1 is substituted with an amino acid other than glutamic acid, and one or more amino acids are deleted, substituted or added, (x) the polypeptide according to the above (viii) or (ix), wherein the amino acid other than glutamic acid is a basic amino acid, (xi) the polypeptide according to the above (viii) or (ix), wherein the amino acid other than glutamic acid is lysine, and the like.

The microorganism belonging to a coryneform bacterium according to the present invention means a microorganism which is defined in *Bergeys Manual of Determinative Bacteriology*, 8, 599 (1974), and examples of the microorganism include a microorganism belonging to the genus *Corynebacterium*, the genus *Brevibacterium* or the genus *Microbacterium*.

Specific examples include *Corynebacterium acetoacidophilum*, *Corynebacterium acetoglutamicum*, *Corynebacterium callunae*, *Corynebacterium glutamicum*, *Corynebacterium herculis*, *Corynebacterium lilium*, *Corynebacterium melassecola*, *Corynebacterium thermoaminogenes*, *Corynebacterium efficiens*, *Corynebacterium diphtheriae*, *Brevibacterium saccharolyticum*, *Brevibacterium immariophilum*, *Brevibacterium roseum*, *Brevibacterium thiogenitalis*, *Microbacterium ammoniaphilum* and the like.

More specific examples include *Corynebacterium acetoacidophilum* ATCC 13870, *Corynebacterium acetoglutamicum* ATCC 15806, *Corynebacterium callunae* ATCC 15991, *Corynebacterium glutamicum* ATCC 13032, *Corynebacterium glutamicum* ATCC 13060, *Corynebacterium glutamicum* ATCC 13826 (former genus and species: *Brevibacterium flavum* or *Corynebacterium lactofermentum*), *Corynebacterium glutamicum* ATCC 14020 (former genus and species: *Brevibacterium divaricatum*), *Corynebacterium glutamicum* ATCC 13869 (former genus and species: *Brevibacterium lactofermentum*), *Corynebacterium herculis* ATCC 13868, *Corynebacterium lilium* ATCC 15990, *Corynebacterium melassecola* ATCC 17965, *Corynebacterium thermoaminogenes* ATCC 9244, *Corynebacterium efficiens* YS-314, *Corynebacterium diphtheriae* NCTC 13129, *Brevibacterium saccharolyticum* ATCC 14066, *Brevibacterium immariophilum* ATCC 14068, *Brevibacterium roseum* ATCC 13825, *Brevibacterium thiogenitalis* ATCC 19240, *Microbacterium ammoniaphilum* ATCC 15354 and the like.

The above-mentioned glutamine synthetase 2 derived from a microorganism belonging to a coryneform bacterium may be any glutamine synthetase 2, so long as it is the above-mentioned glutamine synthetase 2 derived from a microorganism belonging to a coryneform bacterium, and examples include a glutamine synthetase 2 derived from *Corynebacterium glutamicum* ATCC 13032, described in EP 1108790 and which have the amino acid sequence of SEQ ID NO:1, a glutamine synthetase 2 derived from *Corynebacterium efficiens* YS-314, which has the amino acid sequence described in GenBank accession number NP_738737, a glutamine synthetase 2 derived from *Corynebacterium diphtheriae* NCTC 13129, which has the amino acid sequence described in GenBank accession number NP_940011, and the like.

The number of amino acids which is deleted, substituted or added according to the polypeptide of the present invention in the above-described (i) is not particularly limited, but is such a number that the deletion, substitution or addition can be carried out by a known method such as the site-directed mutagenesis which is described later, namely, from 1 to several tens, preferably from 1 to 20, more preferably from 1 to 10, and most preferably from 1 to 5.

In addition, "one or more amino acids are deleted, substituted or added" means that there is deletion, substitution or addition of one or plural amino acids at optional positions in the same sequence, wherein the deletion, substitution or addition may occur at the same time and the amino acid which is substituted or added may be either a natural type or an unnatural type. The natural type amino acid includes L-alanine, L-asparagine, L-aspartic acid, L-arginine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Examples of mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine The polypeptide of the present invention in the above-described (i) preferably has a homology of at least 70% or more, more preferably 90% or more, still more preferably 95% or more, particularly preferably 98% or more, and most preferably 99% or more, with the amino acid sequence of SEQ ID NO:1.

Homology of amino acid sequences and nucleotide sequences can be determined using, for example, algorithm BLAST [*Pro. Natl. Acad. Sci. USA*, 90, 5873 (1993)] or FASTA [*Methods in Enzymol.*, 183, 63 (1990)] by Karlin and Altschul. Based on this algorithm BLAST, the programs called BLASTN and BLASTX were developed [*J. Mol. Biol.*, 215, 403 (1990)]. When a nucleotide sequence is analyzed by BLASTN based on BLAST, the parameters are set to, for example, Score=100, wordlength=12. Also, when an amino acid sequence is analyzed by BLASTX based on BLAST, the parameters are set to, for example, score=50, wordlength=3. When the BLAST and Capped BLAST programs are used, the default parameters of each program are used. Specific techniques of these analytical methods are conventionally known.

In expressing a polypeptide comprising an amino acid sequence in which one or more amino acids are deleted, substituted or added in the amino acid sequence of a glutamine synthetase 2 derived from a microorganism belonging to a coryneform bacterium, the wild type coryneform bacterium to be used as a host means a type of microorganism in a wild population, which is most frequently found in the species to which the microorganism belongs, and examples include *Corynebacterium acetoacidophilum* ATCC 13870, *Corynebacterium acetoglutamicum* ATCC 15806, *Corynebacterium callunae* ATCC 15991, *Corynebacterium glutamicum* ATCC 13032, *Corynebacterium glutamicum* ATCC 13060, *Corynebacterium glutamicum* ATCC 13826 (former genus and species: *Brevibacterium flavum* or *Corynebacterium lactofermentum*), *Corynebacterium glutamicum* ATCC 14020 (former genus and species: *Brevibacterium divaricatum*), *Corynebacterium glutamicum* ATCC 13869 (former genus and species: *Brevibacterium lactofermentum*), *Corynebacterium herculis* ATCC 13868, *Corynebacterium lilium* ATCC 15990, *Corynebacterium melassecola* ATCC 17965, *Corynebacterium thermoaminogenes* ATCC 9244, *Brevibacterium saccharolyticum* ATCC 14066, *Brevibacterium immariophilum* ATCC 14068, *Brevibacterium roseum* ATCC 13825, *Brevibacterium thiogenitalis* ATCC 19240, *Microbacterium ammoniaphilum* ATCC 15354 and the like.

The method for expressing a polypeptide comprising an amino acid sequence in which one or more amino acids are deleted, substituted or added in the amino acid sequence of a glutamine synthetase 2 derived from a microorganism belonging to a coryneform bacterium by using a wild type coryneform bacterium as a host cell includes a method in which the polypeptide is expressed by introducing a DNA encoding the polypeptide into a wild type coryneform bacterium, and substituting the DNA and a DNA encoding a wild type glutamine synthetase 2 on the chromosomal DNA of a wild type coryneform bacterium by a homologous recombination technique, a method in which the polypeptide is expressed by transforming a wild type coryneform bacterium with a recombinant DNA comprising a DNA encoding the polypeptide, and the like.

The polypeptide comprising an amino acid sequence in which one or more amino acids are deleted, substituted or added in the amino acid sequence of a glutamine synthetase 2 derived from a microorganism belonging to a coryneform bacterium, wherein a production amount of L-glutamine when the polypeptide is expressed by using a wild type coryneform bacterium as a host cell is larger than that of the wild type coryneform bacterium can be confirmed by measuring that the amount of L-glutamine produced by a transformant in which the polypeptide was expressed by introducing a DNA encoding the polypeptide into a wild type coryneform bacterium and substituting the DNA for a DNA encoding a wild type glutamine synthetase 2 on the chromosomal DNA of a wild type coryneform bacterium by a homologous recombination technique, or by a transformant in which the polypeptide was expressed by transforming a wild type coryneform bacterium with a recombinant DNA comprising a DNA encoding the polypeptide, is larger than that of the wild type coryneform bacterium.

Specifically, a transformant in which the polypeptide was expressed by introducing a DNA encoding the polypeptide into a *Corynebacterium glutamicum* wild strain, *Corynebacterium glutamicum* ATCC 13032, and substituting the DNA for a DNA on the chromosomal DNA of *Corynebacterium glutamicum* ATCC 13032, encoding a wild type glutamine synthetase 2, by a homologous recombination technique, or a transformant in which *Corynebacterium glutamicum* ATCC 13032 was transformed with a recombinant DNA comprising a DNA encoding the polypeptide and a vector such as pCS299P (WO 00/63388), is constructed. The transformant and *Corynebacterium glutamicum* ATCC 13032 are cultured at 30° C. for 24 hours in a BYG agar medium [a medium containing 10 g of glucose, 7 g of meat extract, 10 g of peptone, 3 g of sodium chloride, 5 g of yeast extract (manufactured by Difco) and 18 g of Bacto-Agar (manufactured by Difco) in 1 liter of water and adjusted to pH 7.2], and each strain was inoculated into a test tube containing 6 ml of a seed culture medium [a medium containing 50 g of glucose, 20 g of bouillon, 5 g of ammonium sulfate, 5 g of urea, 2 g of potassium dihydrogen phosphate, 0.5 g of magnesium sulfate heptahydrate, 1 mg of iron sulfate heptahydrate, 0.4 mg of copper sulfate pentahydrate, 0.9 mg of zinc sulfate heptahydrate, 0.07 mg of manganese chloride tetrahydrate, 0.01 mg of disodium tetraborate, 0.04 mg of hexaammonium heptamolybdate, 0.5 mg of thiamine hydrochloride and 0.1 mg of biotin in 1 liter of water and adjusted to pH 7.2, followed by addition of 10 g of calcium carbonate] and cultured at 30° C. for 12 hours to 16 hours. Each of the thus obtained seed cultures is inoculated, at an inoculum concentration of 10%, into a 300 ml capacity conical flask with baffles containing 30 ml of a main culture medium (a medium containing 50 g of glucose, 2 g of urea, 20 g of ammonium sulfate, 0.5 g of potassium dihydrogen phosphate, 0.5 g. of dipotassium hydrogen phosphate, 0.5 g of magnesium sulfate heptahydrate, 2 mg of iron sulfate heptahydrate, 2.5 mg of manganese chloride tetrahydrate, 0.5 mg of thiamine hydrochloride and 0.1 mg or 0.001 mg of biotin in 1 liter of water and adjusted to pH 7.2, followed by addition of 20 g of calcium carbonate) and cultured for 16 to 18 hours before the sugar is not completely consumed under conditions at 30° C. and 220 rpm. By removing the cells from the thus obtained culture by centrifugation, an accumulated amount of L-glutamine in the supernatant is determined by high performance liquid chromatography (HPLC). It can be confirmed by measuring that the accumulated amount of L-glutamine in the supernatant obtained by culturing the transformant is larger than the accumulated amount of L-glutamine in the supernatant obtained by culturing *Corynebacterium glutamicum* ATCC 13032.

In the polypeptides of the present invention in the above-mentioned (ii) to (vi), the amino acid at a position corresponding to the amino acid at position 64 from the N-terminal in the amino acid sequence of SEQ ID NO:1 in the glutamine synthetase 2 derived from a microorganism belonging to a coryneform bacterium means an amino acid at a position corresponding to the amino acid at position 64 from the N-terminal in the amino acid sequence of SEQ ID NO:1 in the amino acid sequence of the glutamine synthetase 2 derived from a microorganism belonging to a coryneform bacterium, when the homology of the amino acid sequence of the glutamine synthetase 2 derived from a microorganism belonging to a coryneform bacterium with the amino acid sequence of SEQ ID NO:1 is calculated using a homology analyzing program, such as the above-mentioned BLAST and FASTA, and parameters, and the two amino acid sequences are aligned.

The amino acid other than glutamic acid may be any amino acid other than glutamic acid, but is preferably an amino acid selected from alanine, glycine, valine, leucine, isoleucine, cysteine, methionine, tryptophan, phenylalanine, proline, lysine, histidine, arginine, aspartic acid, asparagine, glutamine, serine, threonine and tyrosine, more preferably a basic amino acid, still more preferably an amino acid selected from lysine, histidine and arginine, and most preferably lysine.

By the above-mentioned method, it can be confirmed that the production amount of L-glutamine by expressing the polypeptide comprising an amino acid sequence in which, in the amino acid sequence of the glutamine synthetase 2, the amino acid at a position corresponding to the amino acid at position 64 from the N-terminal in the amino acid sequence of SEQ ID NO:1 is substituted with an amino acid other than glutamic acid using a wild type coryneform bacterium as a host, is larger than that of the wild type coryneform bacterium.

Each of the polypeptides of the present invention in the above-mentioned (iii) to (vi) is a polypeptide comprising an amino acid sequence encoded by a DNA which can be obtained by deleting, substituting or adding a nucleotide on the DNA encoding the polypeptide of the present invention in the above-mentioned (i) or (ii) using the site-directed mutagenesis which is described later. The site-directed mutation to be introduced may be any mutation, so long as one or more amino acids other than an amino acid at a position corresponding to the amino acid at position 64 from the N-terminal in the amino acid sequence of SEQ ID NO:1 are deleted, substituted or added.

The amino acid which is deleted, substituted or added is not particularly limited, so long as it is an amino acid other than the amino acid at a position corresponding to the amino acid at position 64 from the N-terminal in the amino acid sequence of SEQ ID NO:1.

In addition, "one or more amino acids are deleted, substituted or added" means that there are one or plural of deletion, substitution or addition at optional positions other than the amino acid at a position corresponding to the amino acid at position 64 from the N-terminal in the amino acid sequence of SEQ ID NO:1, wherein the deletion, substitution or addition may occur at the same time and the amino acid which is substituted or added may be either a natural type or a non-natural type, and the substitutable amino acids are similar to the above.

The polypeptides in the above-described (iii) to (vi) preferably have a homology of at least 70% or more, more preferably 90% or more, still more preferably 95% or more, particularly preferably 98% or more, and most preferably 99% or more, with the amino acid sequence of SEQ ID NO:1.

The above-mentioned polypeptide (vii) of the present invention is a polypeptide comprising an amino acid sequence in which one or more amino acids are deleted, substituted or added in the amino acid sequence of SEQ ID NO:1, wherein a production amount of L-glutamine when the polypeptide is expressed by using a wild type coryneform bacterium as a host cell is larger than that of the wild type coryneform bacterium.

The number of amino acids which are deleted, substituted or added is not particularly limited, but is such a number that the deletion, substitution or addition can be carried out by a known method such as the above-mentioned site-directed mutagenesis, namely, from 1 to several tens, preferably from 1 to 20, more preferably from 1 to 10, and most preferably from 1 to 5.

In addition, "one or more amino acids are deleted, substituted or added" means that there are one or plural of deletion, substitution or addition at optional positions in the same sequence, wherein the deletion, substitution or addition may occur at the same time and the amino acid which is substituted or added may be either a natural type or an unnatural type, and the substitutable amino acids are similar to the above.

The polypeptide of the present invention in the above-described (vii) preferably has a homology of 70% or more, more preferably 90% or more, still more preferably 95% or more, particularly preferably 98% or more, and most preferably 99% or more, with the amino acid sequence of SEQ ID NO:1.

The above-described polypeptides (viii) to (xi) of the present invention can be prepared using a DNA in which a codon encoding glutamic acid at position 64 from the N-terminal in the amino acid sequence of SEQ ID NO:1 is substituted with a codon encoding an amino acid other than glutamic acid using a DNA encoding the amino acid sequence of SEQ ID NO:1, by the site-directed mutagenesis which is described later. The amino acid other than glutamic acid includes the above-mentioned amino acids.

Each of the polypeptides of the present invention in the above-mentioned (ix) to (xi) is a polypeptide comprising an amino acid sequence encoded by a DNA which can be obtained by deleting, substituting or adding a nucleotide on the DNA encoding the polypeptide of the present invention in the above-mentioned (vi) or (vii) using the site-directed mutagenesis which is described later. The site-directed mutation to be introduced may be any mutation, so long as one or more amino acids other than the amino acid at a position that corresponds to glutamic acid at position 64 from the N-terminal in the amino acid sequence of SEQ ID NO:1 in the polypeptide of the present invention in the above-mentioned (vi) or (vii) are deleted, substituted or added.

The amino acid which is deleted, substituted or added is not particularly limited, so long as it is an amino acid other than glutamic acid at position 64 from the N-terminal in the amino acid sequence of SEQ ID NO:1.

In addition, "one or more amino acids are deleted, substituted or added" means that there are one or plural of deletion, substitution or addition at optional positions other than glutamic acid at position 64 from the N-terminal in the amino acid sequence of SEQ ID NO:1, wherein the deletion, substitution or addition may occur at the same time and the amino acid which is substituted or added may be either a natural type or a non-natural type, and the substitutable amino acids are similar to the above.

The polypeptides in the above-described (ix) to (xi) preferably have a homology of 70% or more, more preferably 90% or more, sill more preferably 95% or more, particularly preferably 98% or more, and most preferably 99% or more, with the amino acid sequence of SEQ ID NO:1.

(2) DNA of the Present Invention

The DNA of the present invention includes:
(i) a DNA encoding any polypeptide of the above polypeptides of the present invention,
(ii) the DNA according to the above (i), which comprises a nucleotide sequence in which, in the nucleotide sequence of a DNA encoding the glutamine synthetase 2 derived from a microorganism belonging to a coryneform bacterium, a region corresponding to the nucleotide sequence at positions 190 to 192 from the 5'-terminal in the nucleotide sequence of SEQ ID NO:2 is a codon encoding an amino acid other than glutamic acid,
(iii) the DNA according to the above (ii), wherein the codon encoding an amino acid other than glutamic acid is a codon encoding a basic amino acid,
(iv) the DNA according to the above (ii), wherein the codon encoding an amino acid other than glutamic acid is a codon encoding lysine,
(v) the DNA according to any one of the above (ii) to (iv), wherein the microorganism belonging to a coryneform bacterium is a microorganism belonging to the genus *Corynebacterium*, the genus *Brevibacterium* or the genus *Mycobacterium*,
(vi) the DNA according to the above (i), wherein the nucleotide sequence at positions 190 to 192 from the 5'-terminal in the nucleotide sequence of SEQ ID NO:2 comprises a codon encoding an amino acid other than glutamic acid,
(vii) the DNA according to the above (vi), wherein the codon encoding an amino acid other than glutamic acid is a codon encoding a basic amino acid, (viii) the DNA according to the above (vi), wherein the codon encoding an amino acid other than glutamic acid is a codon encoding lysine, (ix) a DNA which hybridizes with a DNA consisting of a nucleotide sequence complementary to the nucleotide sequence of SEQ ID NO:2 under stringent conditions, and comprises a nucleotide sequence in which a region corresponding to the nucleotide sequence at positions 190 to 192 from the 5'-terminal in the nucleotide sequence of SEQ ID NO:2 is a codon encoding an amino acid other than glutamic acid, wherein a production amount of L-glutamine by a transformant obtained by introducing the DNA into a wild type coryneform bacterium is larger than that of the wild type coryneform bacterium, (x) the DNA according to the above (ix), wherein the codon encoding an amino acid other than glutamic acid is a codon encoding a basic amino acid, (xi) the DNA according to the above (ix), wherein the codon encoding an amino acid other than glutamic acid is a codon encoding lysine, (xii) a recombinant DNA which comprises the DNA according to any one of the above (i) to (xi), and the like.

The above-mentioned DNA (i) of the present invention is a DNA encoding the polypeptide of the present invention in the above-mentioned (1), and examples include a DNA encoding a polypeptide comprising an amino acid sequence in which one or more amino acids are deleted, substituted or added in the amino acid sequence of the glutamine synthetase 2 derived from a microorganism belonging to a coryneform bacterium, wherein a production amount of L-glutamine when the polypeptide is expressed by using a wild type coryneform bacterium as a host cell is larger than that of the wild type coryneform bacterium.

The DNA encoding the glutamine synthetase 2 derived from a microorganism belonging to a coryneform bacterium among the above-mentioned DNA (ii) to (v) of the present invention includes the DNA encoding the glutamine synthetase 2 derived from a microorganism belonging to a coryneform bacterium according to the above-mentioned (1).

The DNA encoding the glutamine synthetase 2 derived from a microorganism belonging to a coryneform bacterium may be any DNA, so long as it is the DNA encoding the glutamine synthetase 2 derived from a microorganism belonging to a coryneform bacterium according to the above-mentioned (1), and the DNA encoding the glutamine synthetase 2 derived from a microorganism belonging to a coryneform bacterium includes, for example, a DNA comprising the nucleotide sequence of SEQ ID NO:2 described in EP 1108790, a DNA comprising a nucleotide sequence complementary to the nucleotide sequence at positions 2258903 to 2260453 in *Corynebacterium efficiens* YS-3,4-derived chromosomal DNA, described in GenBank accession number BA000035, a DNA comprising a nucleotide sequence complementary to the nucleotide sequence at positions 320981 to 322321 in *Corynebacterium diphtheriae* NCTC 13129-derived chromosomal DNA, described in GenBank accession number BX248358, and the like.

In the nucleotide sequence of DNA encoding the glutamine synthetase 2 derived from a microorganism belonging to a coryneform bacterium, the region corresponding to the nucleotide sequence at positions 190 to 192 in the nucleotide sequence of SEQ ID NO:2 means a region corresponding to positions 190 to 192 in the nucleotide sequence of SEQ ID NO:2 in the nucleotide sequence possessed by the DNA encoding the glutamine synthetase 2 derived from a microorganism belonging to a coryneform bacterium, when homology of the nucleotide sequence possessed by the DNA encoding the glutamine synthetase 2 derived from a microorganism belonging to a coryneform bacterium with the nucleotide sequence of SEQ ID NO:2 is calculated using homology analyzing programs, such as the above-mentioned BLAST and FASTA, and parameters, and the two nucleotide sequences are aligned.

The codon encoding an amino acid other than glutamic acid, in the region corresponding to positions 190 to 192 from the 5'-terminal in the nucleotide sequence of SEQ ID NO:2, may be any codon encoding an amino acid other than glutamic acid, but is preferably a codon encoding an amino acid selected from alanine, glycine, valine, leucine, isoleucine, cysteine, methionine, tryptophan, phenylalaninc, prolinc, lysine, histidine, arginine, aspartic acid, asparagine, glutamine, serine, threonine and tyrosine, more preferably a basic amino acid, still more preferably an amino acid selected from lysine, histidine and arginine, and most preferably lysine.

The fact that the production amount of L-glutamine when the polypeptides encoded by the DNA of the above-mentioned (ii) to (v) are expressed by using a wild type coryneform bacterium as a host cell is larger than that of the wild type coryneform bacterium can be confirmed by a method similar to the above-mentioned method. That is, such fact can be confirmed by obtaining a transformant in which the polypeptide is expressed by introducing the DNA into a wild type coryneform bacterium and substituting the DNA for a DNA encoding a wild type glutamine synthetase 2 on the chromosomal DNA of a wild type coryneform bacterium by a homologous recombination technique, or a transformant in which the polypeptide was expressed by transforming a wild type coryneform bacterium with a recombinant DNA comprising the DNA, and measuring that the production amount of L-glutamine in a culture supernatant when the transformant is cultured in a medium is larger than that of when the wild type coryneform bacterium as a host cell is cultured in a medium.

The DNA of the present invention in the above-mentioned (vi) to (viii) is a DNA comprising the nucleotide sequence of SEQ ID NO:2, in which a nucleotide sequence at positions 190 to 192 from the 5'-terminal in the nucleotide sequence of SEQ ID NO:2 is substituted with a codon encoding an amino acid other than glutamic acid. The codon includes the above-mentioned codon encoding an amino acid other than glutamic acid.

The fact that the production amount of L-glutamine when the polypeptides encoded by the DNA of the above-mentioned (vi) to (vii) are expressed by using a wild type coryneform bacterium as a host cell is larger than that of the wild type coryneform bacterium can be confirmed by obtaining a transformant in which the polypeptide was expressed by introducing the DNA into a wild type coryneform bacterium and substituting the DNA for a DNA encoding a wild type glutamine synthetase 2 on the chromosomal DNA of a wild type coryneform bacterium by a homologous recombination technique, or a transformant in which a polypeptide having an amino acid encoded by the DNA is expressed by transforming a wild type coryneform bacterium with a recombinant DNA comprising the DNA, and measuring that the production amount of L-glutamine in a culture supernatant when the transformant is cultured in a medium is larger than that of when the wild type coryneform bacterium as a host cell is cultured. A specific method is as described above.

In the DNA of the above-mentioned (ix) to (xi), the DNA which hybridizes with a DNA comprising a nucleotide sequence complementary to the nucleotide sequence of SEQ ID NO:2 under stringent conditions means a DNA which is obtained by using a part or full portion of a complementary chain of the DNA comprising the nucleotide sequence of SEQ ID NO:2 as a probe according to the method using colony hybridization, plaque hybridization, Southern blot hybridization or the like, and specific examples include a DNA which can be identified by carrying out hybridization at 65° C. using a filter to which a colony- or plaque-derived DNA is immobilized, in the presence of 0.7 to 1.0 mol/l of sodium chloride, and then washing the filter under a condition of 65° C. using from 0.1 to 2-fold concentration of SSC solution (composition of the 1-fold concentration of SSC solution contains 150 mmol/l sodium chloride and 15 mmol/l sodium citrate). The hybridization can be carried out in accordance with the methods described in *Molecular Cloning, A Laboratory Manual*, Third Edition, Cold Spring Harbor Laboratory Press (2001) (hereinafter referred to as *Molecular Cloning*, 3rd edition), *Current Protocols in Molecular Biology*, John Willey & Sons (1987-1997) (hereinafter referred to as *Current Protocols in Molecular Biology*), *DNA Cloning* 1: *Core Techniques, A Practical Approach*, Second Edition, Oxford University (1995) and the like. Specifically, the hybridizable DNA is a DNA having a homology of at least 70% or more, preferably 90% or more, more preferably 95% or more, particularly preferably 98% or more, and most preferably 99% or more, with the nucleotide sequence of SEQ ID NO:2, when calculated using BLAST, FASTA or the like.

In the above-mentioned hybridizable DNA, the codon in the DNA comprising a nucleotide sequence in which a region corresponding to a nucleotide sequence at positions 190 to 192 from the 5'-terminal in the nucleotide sequence of SEQ ID NO:2 is a codon encoding an amino acid other than glutamic acid includes the above-mentioned codon encoding an amino acid other than glutamic acid.

The fact that the production amount of L-glutamine when the polypeptide encoded by the DNA is expressed by using a wild type coryneform bacterium as a host cell is larger than that of the wild type coryneform bacterium can be confirmed by the above-mentioned method.

The DNA of the present invention includes, for example, a DNA in which guanine at position 190 from the 5'-terminal in the nucleotide sequence of SEQ ID NO:2 is substituted with adenine, and the like. The DNA is a DNA encoding a polypeptide comprising an amino acid sequence in which the amino acid at position 64 from the N-terminal in the amino acid sequence of SEQ ID NO:1 is substituted with lysine.

The above-mentioned recombinant DNA (xii) of the present invention is a recombinant DNA comprising the DNA of the present invention in the above-mentioned (i) to (xi) and a vector. The vector includes a plasmid, a cosmid, a bacteriophage and the like, and it may be any vector, so long as it can be ligated with the DNA of the present invention in the above mentioned (i) to (xi). The plasmid includes pUC19 (manufactured by Takara Bio), pHSG299 (manufactured by Takara Bio), pBR322 (manufactured by Takara Bio), pCG1 (Japanese Published Unexamined Patent Application No. 134500/82), pCG2 (Japanese Published Unexamined Patent Application No. 35197/83), pCG4 (Japanese Published Unexamined Patent Application No. 183799/82), YEp13 (ATCC 37115), YEp24 (ATCC 37051), YCp50 (ATCC 37419) and the like. The cosmid includes pAxCAwtit (manufactured by Nippon Gene) and the like, and the bacteriophage includes M13mp18RF (manufactured by Nippon Gene) and the like.

(3) Preparation of the DNA of the Present Invention
(i) Preparation of a DNA Encoding a Glutamine Synthetase 2 Derived from a Microorganism Belonging to a Coryneform Bacterium As a method for preparing a DNA encoding a glutamine synthetase 2 derived from a microorganism belonging to a coryneform bacterium, the DNA can be obtained from a microorganism belonging to a coryneform bacterium by PCR or the like using a chromosomal DNA as a template which can be prepared in accordance with the method of Saito et al. [*Biochim. Biophys. Acta*, 72, 619 (1963)] and using a primer DNA which can be designed and synthesized based on the nucleotide sequence of SEQ ID NO:2.

As a method for preparing a DNA encoding a glutamine synthetase 2 derived from a microorganism belonging to a coryneform bacterium wherein a full nucleotide sequence of the chromosomal DNA has been found, the DNA can be obtained by PCR or the like as described above by using the chromosomal DNA as a template and using a primer DNA which can be designed and synthesized based on the nucleotide sequence of a DNA encoding a polypeptide having a homology of 70% or more with a polypeptide comprising the amino acid sequence of SEQ ID NO:1.

Specifically, a DNA encoding a glutamine synthetase 2 can be obtained by preparing chromosomal DNA from *Corynebacterium glutamicum* ATCC 13032, chemically synthesizing, using the DNA as a template, DNA fragments respectively having sequences of the 5'-terminal and 3'-terminal regions of the nucleotide sequence of SEQ ID NO:2, and carrying out PCR using the DNA fragments as a primer set. The DNA which can be obtained by the above-mentioned method includes a DNA comprising the nucleotide sequence of SEQ ID NO:2, and the like.

The DNA encoding a glutamine synthetase 2 derived from a microorganism belonging to a coryneform bacterium can also be obtained by a hybridization method which uses a part or full portion of the DNA comprising the nucleotide sequence of SEQ ID NO:2 as a probe.

In addition, the DNA encoding a glutamine synthetase 2 derived from a microorganism belonging to a coryneform bacterium can also be obtained, based on the nucleotide sequence of SEQ ID NO:2, by chemically synthesizing a DNA comprising the nucleotide sequence by a known method.

(ii) Preparation of the DNA of the Present Invention
The DNA of the present invention can be obtained by a usual method using the DNA encoding a glutamine synthetase 2 derived from a microorganism belonging to a coryneform bacterium obtained by the above-mentioned (i).

A DNA encoding a polypeptide comprising an amino acid sequence in which one or more amino acids are deleted, substituted or added in the amino acid sequence of a glutamine synthetase 2 derived from a microorganism belonging to a coryneform bacterium can be easily obtained, for example, by introducing a site-directed mutation into a DNA encoding a polypeptide comprising the amino acid sequence of SEQ ID NO:1 using the site-directed mutagenesis described in *Molecular Cloning*, 3rd edition, *Current Protocols in Molecular Biology, Nucleic Acids Research*, 10, 6487 (1982), *Proc. Natl. Acad. Sci. USA*, 79, 6409 (1982), *Gene*, 34, 315 (1985), *Nucleic Acids Research*, 13, 4431 (1985), *Proc. Natl. Acad. Sci. USA*, 82, 488 (1985) and the like.

A coryneform bacterium which produces a polypeptide comprising an amino acid sequence in which one or more amino acids are deleted, substituted or added in the amino acid sequence of a glutamine synthetase 2 derived from a microorganism belonging to a coryneform bacterium can be obtained by transforming a coryneform bacterium which produces a wild type glutamine synthetase 2 with a DNA encoding the polypeptide, and substituting the DNA encoding the polypeptide which can be obtained by the above-mentioned method for the DNA encoding the wild type glutamine synthetase 2 using a homologous recombination technique. In addition, it can also be obtained by transforming a coryneform bacterium with a recombinant DNA which comprises the DNA encoding the polypeptide which can be obtained by the above-mentioned method.

The fact that the production amount of L-glutamine when the polypeptide encoded by a DNA which can be obtained by the above-mentioned method is expressed by using a wild type coryneform bacterium as a host cell is larger than that of the wild type coryneform bacterium can be confirmed by the above-mentioned method.

The following method can also be mentioned as a method for obtaining a DNA encoding a mutation type glutamine synthetase 2 comprising an amino acid sequence in which one or more amino acids are deleted, substituted or added in the amino acid sequence of a glutamine synthetase 2 derived from a microorganism belonging to a coryneform bacterium, wherein a production amount of L-glutamine when the polypeptide is expressed by using a wild type coryneform bacterium as a host cell is larger than that of the wild type coryneform bacterium.

A library of mutated glutamine synthetase 2 genes is constructed by introducing random mutations into the DNA encoding the glutamine synthetase 2 derived from a microorganism belonging to a coryneform bacterium by a method for contacting with a chemical mutagen agent such as hydroxylamine or an error prone PCR method. A recombinant DNA is constructed by ligating the library with a plasmid DNA which can autonomously replicate in a coryneform bacterium and contains a drug-resistance gene which can provide resistance to a drug which inhibits growth of the coryneform bacterium, and then a wild type coryneform bacterium is transformed with the recombinant DNA. The transformant is spread at a density of 1 to 10 cells/cm$^2$ on a minimum agar medium [glucose 1%, NH$_4$Cl 0.4%, urea 0.2%, KH$_2$PO$_4$ 0.1%, K$_2$HPO$_4$ 0.3%, MgSO$_4$ 0.04%, FeSO$_4$ 10 mg/l, MnSO$_4$ 1 mg/l, nicotinic acid 5 mg/l, biotin 100 µg/l, thiamine hydrochloride 5 mg/l, Bacto Agar (Difco) 1.6% (pH 7.2)] containing approximately 1×10$^6$ cells/cm$^3$ of a *Corynebacterium glutamicum* ATCC 13032-derived glnA deficient strain MJ 4-26 which shows glutamine requirement [*FEMS Microbiology Letters,* 154, 81 (1997)]. After allowing the minimum agar medium to stand at 30° C. for 2 to 3 days, haloes which can confirm growth of the glutamine-requiring MJ 4-26 strain on the agar medium are scraped out and applied onto the minimum agar medium containing such a drug on that only transformants comprising the recombinant DNA can grow and form single colonies. The drug-containing minimum agar medium is allowed to stand at 30° C. for 1 to 2 days, and then transformants which formed colonies are selected. Furthermore, each of the transformants is cultured in a medium, and a glutamine concentration in the medium at the time of the completion of the culturing is measured. A transformant showing an increased glutamine concentration in the medium at the time of the completion of the culturing, in comparison with the glutamine concentration detected when a wild type coryneform bacterium is cultured in the same manner, is selected. Since the DNA encoding a mutated glutamine synthetase 2 possessed by the recombinant DNA held by the transformant provides the host with higher L-glutamine productivity than the wild type coryneform bacterium, the DNA of the present invention can be obtained by such a method.

A DNA encoding a polypeptide in which an amino acid at a position corresponding to the amino acid at position 64 from the N-terminal in the amino acid sequence of SEQ ID NO:1 is substituted with an amino acid other than glutamic acid in the amino acid sequence of a glutamine synthetase 2 can be obtained by carrying out a nucleotide substitution by the above-mentioned site-directed mutagenesis in such a manner that the codon encoding an amino acid at a position corresponding to the amino acid at position 64 from the N-terminal in the amino acid sequence of SEQ ID NO:1, in the DNA encoding a polypeptide comprising the amino acid sequence of SEQ ID NO:1, becomes a codon encoding an amino acid other than glutamic acid. The codon encoding an amino acid other than glutamic acid may be any codon encoding an amino acid other than glutamic acid, but is preferably a codon encoding an amino acid selected from alanine, glycine, valine, leucine, isoleucine, cysteine, methionine, tryptophan, phenylalanine, proline, lysine, histidine, arginine, aspartic acid, asparagine, glutamine, serine, threonine and tyrosine, more preferably a basic amino acid, still more preferably an amino acid selected from lysine, histidine and arginine, and most preferably lysine.

The fact that the production amount of glutamine when a polypeptide encoded by a DNA which can be obtained by the above-mentioned method is expressed by using a wild type coryneform bacterium as a host cell is larger than that of the wild type coryneform bacterium can be confirmed by the above-mentioned method.

Using a DNA encoding a polypeptide comprising the amino acid sequence of SEQ ID NO:1, the above-mentioned site-directed mutagenesis, a method of contacting with a chemical mutagen, a method of introducing a mutation by an error prone PCR method and the like can be used for obtaining a DNA encoding a polypeptide comprising an amino acid sequence in which one or more amino acids are deleted, substituted or added in the amino acid sequence of SEQ ID NO:1, wherein a production amount of L-glutamine when the polypeptide is expressed by using a wild type coryneform bacterium as a host cell is larger than that of the wild type coryneform bacterium. The existence of the DNA of the present invention can be confirmed by comparing the glutamine production by the above-mentioned method.

A DNA encoding a polypeptide comprising an amino acid sequence in which the amino acid at position 64 from the N-terminal in the amino acid sequence of SEQ ID NO:1 is substituted with an amino acid other than glutamic acid can be obtained by carrying out a nucleotide substitution by the above-mentioned site-directed mutagenesis in such a manner that the codon encoding glutamic acid at position 64 from the N-terminal in the amino acid sequence of SEQ ID NO:1, in the DNA encoding a polypeptide comprising the amino acid sequence of SEQ ID NO:1, becomes a codon encoding an amino acid other than glutamic acid. The codon includes the above-mentioned codon encoding an amino acid other than glutamic acid.

The fact that the production amount of glutamine when a polypeptide encoded by a DNA which can be obtained by the above-mentioned method is expressed by using a wild type coryneform bacterium as a host cell is larger than that of the wild type coryneform bacterium can be confirmed by the above-mentioned method.

In preparing a DNA encoding a polypeptide comprising an amino acid sequence in which one or more amino acids other than an amino acid at a position corresponding to the amino acid at position 64 from the N-terminal in the amino acid sequence of SEQ ID NO:1 are deleted, it is preferable to delete a codon other than the codon encoding the amino acid in a codon unit, namely 3 nucleotides. Also, in preparing a DNA encoding a polypeptide comprising an amino acid sequence in which one or more amino acids other than the amino acid at a position corresponding to the amino acid at position 64 from the N-terminal in the amino acid sequence of SEQ ID NO:1 are substituted, it is preferable to carry out nucleotide substitution in such a manner that, in a nucleotide other than the nucleotide contained in the codon encoding the amino acid at position 64 from the N-terminal in the amino acid sequence of SEQ ID NO:1, the amino acid encoded by the codon containing the nucleotide is substituted by another amino acid. In addition, in preparing a DNA encoding a polypeptide comprising an amino acid sequence in which one or more amino acids are added in the amino acid sequence of the polypeptide of the present invention, it is preferable to add a codon encoding an amino acid, namely 3 nucleotides, between each amino acid-encoding codon or therebefore and thereafter.

The DNA of the present invention can also be obtained using a part or full portion of a complementary chain of the DNA comprising the nucleotide sequence of SEQ ID NO:2 as a probe under stringent conditions by using colony hybridization, plaque hybridization, Southern blot hybridization or the like. Specifically, a DNA, which can be identified by carrying out hybridization at 65° C. using a filter to which a colony- or plaque-derived DNA is immobilized, in the presence of 0.7 to 1.0 mol/l of sodium chloride, and then washing the filter under a condition of 65° C. using from 0.1 to 2-fold concentration of SSC solution (composition of the 1-fold concentration of SSC solution containing 150 mmol/l sodium chloride and 15 mmol/l sodium citrate) can be obtained. The hybridization can be carried out in accordance with the methods described in *Molecular Cloning*, 3rd edition, *Current Protocols in Molecular Biology, DNA Cloning 1: Core Techniques, A Practical Approach*, Second Edition, Oxford University (1995) and the like. The stringent conditions can be adjusted according to the chain length and GC content of the probe DNA and can be set by the method described in *Molecular Cloning*, 3rd edition or the like.

The DNA of the present invention can be obtained by confirming that the above-mentioned DNA obtained by the colony hybridization or the like is a DNA comprising a nucleotide sequence in which a region corresponding to the nucleotide sequence at positions 190 to 192 from the 5'-terminal in the nucleotide sequence of SEQ ID NO:2 is a codon encoding an amino acid other than glutamic acid and by preparing a transformant in which the polypeptide is expressed by introducing the DNA into a wild type coryneform bacterium and substituting the DNA for a DNA encoding a wild type glutamine synthetase 2 on the chromosomal DNA of a wild type coryneform bacterium by a homologous recombination technique, or a transformant in which the polypeptide is expressed by transforming a wild type coryneform bacterium with a recombinant DNA comprising the DNA, and confirming that the production amount of L-glutamine in a culture supernatant when the transformant and a wild type coryneform bacterium as a host cell are cultured in a medium using the above-mentioned method is larger than that of the wild type coryneform bacterium.

The recombinant DNA comprising the DNA of the present invention can be obtained by ligating the DNA of the present invention with a vector. The vector includes a plasmid, a cosmid, a bacteriophage and the like, and it may be any vector thereof, so long as it can be ligated with the DNA of the present invention. The method for ligating the DNA of the present invention with a vector include a method in which the DNA of the present invention is enzymatically ligated to the vector using T4 DNA ligase (manufactured by Takara Bio) or the like, and so on.

(4) Production of the Polypeptide of the Present Invention

The polypeptide of the present invention of the above-described (1) can be produced by expressing the DNA of the present invention of the above-mentioned (2) in a host cell, for example, by the following method in accordance with the methods described in *Molecular Cloning*, 3rd edition, *Current Protocols in Molecular Biology*, and the like.

That is, a DNA fragment having a suitable length and containing a region which encodes the polypeptide, if necessary, is prepared based on the DNA obtained in the above, and a recombinant DNA in which the DNA fragment is ligated to the downstream of the promoter of an appropriate expression vector. By introducing the recombinant DNA into a host cell suitable for the expression vector, a transformant can be prepared.

In addition, the polypeptide of the present invention can be efficiently produced by preparing a DNA in which a nucleotide in the nucleotide sequence of the DNA fragment is substituted to obtain a codon most suitable for the expression of the host cell.

As the host cell, any of bacteria or yeast capable of expressing the gene of interest can be used. As the expression vector, those which can autonomously replicate in the above-mentioned host cell or can be integrated into a chromosome and contain a promoter at such a position that the DNA encoding the polypeptide of the present invention can be transcribed.

When a prokaryote such as a bacterium is used as a host cell, it is preferable that the recombinant vector comprising a DNA encoding the polypeptide of the present invention can perform autonomous replication in the prokaryote and, at the same time, is a vector comprising a promoter, a ribosome binding sequence, the DNA of the present invention and a transcription termination sequence. A gene which controls the promoter may be contained.

The expression vector includes, for example, pBTrp2, pBTac1, pBTac2 (all available from Boehringer Mannheim), pKK233-2 (manufactured by Pharmacia), pSE280 (manufactured by Invitrogen), pGEMEX-1 (manufactured by Promega), pQE-8 (manufactured by QIAGEN), pKYP 10 (Japanese Published Unexamined Patent Application No. 110600/83), pKYP200 [*Agric. Biol. Chem.*, 48, 669 (1984)], pLSA 1 [*Agric. Biol. Chem.*, 53, 277 (1989)], pGEL1 [*Proc. Natl. Acad. Sci. USA*, 82, 4306 (1985)], pBluescript II SK(−) (manufactured by Stratagene), pTrs30 [prepared from *Escherichia coli* JM109/pTrS30 (FERM BP-5403)], pTrs32 [prepared from *Escherichia coli* JM109/pTrS32 (FERM BP-5408)], pGHA2 [prepared from *Escherichia coli* IGHA2 (FERM B-400), Japanese Published Unexamined Patent Application No. 221091/85], pTerm2 (U.S. Pat. No. 4,686, 191, U.S. Pat. No. 4,939,094, U.S. Pat. No. 5,160,735), pSupex, pUB110, pTP5, pC194, pEG400 [*J. Bacteriol.*, 172, 2392 (1990)], pGEX (manufactured by Pharmacia), pET system (manufactured by Novagen) and the like.

The promoter may be any substance, so long as it can function in the host cell. Examples include promoters derived from *Escherichia coli*, phages and the like, such as trp promoter ($P_{trp}$), lac promoter, $P_L$ promoter, $P_R$ promoter and T7 promoter. In addition, artificially designed and modified promoters such as a promoter prepared by ligating two $P_{trp}$ in series ($P_{trp} \times 2$), tac promoter, lacT7 promoter and letI promoter, and the like. It is preferable to use a plasmid in which the space between a ribosome binding sequence, Shine-Dalgarno sequence, and an initiation codon is adjusted to an appropriate distance (e.g., from 6 to 18 nucleotides). According to the recombinant DNA of the present invention, a transcription termination sequence is not always necessary for the expression of the DNA of the present invention, but it is preferred to arrange a transcription terminating sequence immediately downstream of the structural gene.

The host cell includes microorganisms belonging to the genus *Escherichia*, the genus *Serratia*, the genus *Bacillus*, the genus *Brevibacterium*, the genus *Corynebacterium*, the genus *Microbacterium*, the genus *Pseudomonas* and the like. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* GI698, *Escherichia coli* TB1, *Serratia ficaria*, *Serratia fonticola*, *Serratia liquefaciens*, *Serratia marcescens*, *Bacillus subtilis*, *Bacillus amyloliquefaciens*, *Brevibacterium ammoniagenes*, *Brevibacterium immariophilum* ATCC 14068, *Brevibacterium saccharolyticum* ATCC 1869, *Corynebacterium glutamicum* ATCC 13032, *Corynebacterium glutamicum* ATCC 13869, *Corynebacterium acetoacidophilum* ATCC 13870, *Microbacterium ammoniaphilum* ATCC 15354, *Pseudomonas putida*, *Pseudomonas* sp. D-0110 and the like.

Particularly, when the host cell is a microorganism belonging to the genus *Corynebacterium*, the genus *Brevibacterium* or the genus *Microbacterium*, it is preferable to use *Corynebacterium acetoacidophilum*, *Corynebacterium acetoglutamicum*, *Corynebacterium callunae*, *Corynebacterium glutamicum*, *Corynebacterium lactofermentum*, *Corynebacterium herculis*, *Corynebacterium lilium*, *Corynebacterium melassecola*, *Corynebacterium thermoaminogenes*, *Brevibacterium saccharolyticum*, *Brevibacterium immariophilum*, *Brevibacterium roseum*, *Brevibacterium thiogenitalis*, *Microbacterium ammoniaphilum* or the like.

More specifically, it is preferable to use *Corynebacterium acetoacidophilum* ATCC 13870, *Corynebacterium acetoglutamicum* ATCC 15806, *Corynebacterium callunae* ATCC 15991, *Corynebacterium glutamicum* ATCC 13032, *Corynebacterium glutamicum* ATCC 13060, *Corynebacterium glutamicum* ATCC 13826 (former genus and species: *Brevibacterium flavum*), *Corynebacterium glutamicum* ATCC 14020 (former genus and species: *Brevibacterium divaricatum*), *Corynebacterium glutamicum* ATCC 13869 (former genus and species: *Brevibacterium lactofermentum*), *Corynebacterium herculis* ATCC 13868, *Corynebacterium lilium* ATCC 15990, *Corynebacterium melassecola* ATCC 17965, *Corynebacterium thermoaminogenes* ATCC 9244, ATCC 9245, ATCC 9246 and ATCC 9277, *Brevibacterium saccharolyticum* ATCC 14066, *Brevibacterium immariophilum* ATCC 14068, *Brevibacterium roseum* ATCC 13825, *Brevibacterium thiogenitalis* ATCC 19240 or *Microbacterium ammoniaphilum* ATCC 15354.

When the host cell is the above-mentioned microorganism belonging to the genus *Corynebacterium*, the genus *Brevibacterium* or the genus *Microbacterium*, it is preferable to use pCG1 (Japanese Published Unexamined Patent Application No. 134500/82), pCG2 (Japanese Published Unexamined Patent Application No. 35197/83), pCG4 (Japanese Published Unexamined Patent Application No. 183799/82), pCG11 (Japanese Published Unexamined Patent Application No. 134500/82), pCG116, pCE54, pCB101 (all in Japanese Published Unexamined Patent Application No. 105999/83), pCE51, pCE52, pCE53 [all in *Molecular and General Genetics*, 196, 175 (1984)], pCS299P (WO 00/63388) and the like as a vector to be used for preparing a recombinant DNA comprising the DNA of the present invention.

As the method for introducing the recombinant DNA vector, any method which can introduce the DNA into the above-mentioned host cell can be used, and examples include a method which uses calcium ion [*Proc. Natl. Acad. Sci. USA*, 69, 2110, (1972)], a protoplast method (e.g., Japanese Published Unexamined Patent Application No. 186492/82 and Japanese Published Unexamined Patent Application No. 18649/82), or the methods described in *Gene*, 17, 107 (1982) and *Molecular & General Genetics*, 168, 111 (1979), electroporation [e.g., *J. Bacteriology*, 175, 4096 (1993)] and the like.

When yeast is used as a host cell, the expression vector includes, for example, Yep13 (ATCC 37115), Yep24 (ATCC 37051), YCp50 (ATCC 37419), pHS19, pHS15 and the like.

As the promoter, any substance which can function in yeast strains may be used, and it includes, for example, the promoter of a gene of hexokinase or the like in the glycolytic pathway, PHO5 promoter, PGK promoter, GAP promoter, ADH promoter, gal1 promoter, gal10 promoter, heat shock polypeptide promoter, MFα1 promoter, CUP1 promoter and the like.

The host cell includes microorganisms belonging to the genus *Saccharomyces*, the genus *Schizosaccharomyces*, the genus *Kluyveromyces*, the genus *Trichosporon*, the genus *Schwanniomyces*, the genus *Pichia*, the genus *Candida* and the like, such as *Saccharomyces cerevisiae*, *Schizosaccharomyces pombe*, *Kluyveromyces lactis*, *Trichosporon pullulans*, *Schwanniomyces alluvius* and *Candida utilis*.

As the method for introducing the recombinant DNA vector, any method for introducing the DNA into yeast can be used, and it includes, for example, electroporation [*Methods Enzymol*, 194, 182 (1990)], a spheroplast method [*Proc. Natl. Acad. Sci. USA*, 75, 1929 (1978)], a lithium acetate method [*J. Bacteriology*, 153, 163 (1983)], the method described in *Proc. Natl. Acad. Sci. USA*, 75, 1929 (1978) and the like.

When expressed in yeast, a polypeptide to which a sugar or sugar chain is added can be obtained.

As the gene expression method, in addition to the expression as such, it can be expressed as a fusion protein in accordance with the method described in *Molecular Cloning*, 3rd edition, or the like.

The polypeptide of the present invention can be produced by culturing the transformant obtained by the above-mentioned method in a medium to thereby form and accumulate the polypeptide of the present invention in the culture, and recovering the polypeptide of the present invention from the culture.

Culturing of the transformant can be carried out by a usual culturing method.

The medium, as a medium for culturing the transformant, may be either a natural medium or a synthetic medium, so long as it contains a carbon source, a nitrogen source, inorganic salts and the like which can be assimilated by the transformant and can efficiently carry out culturing of the transformant.

As the carbon source, for example, sugars such as glucose, fructose, sucrose, maltose and a starch hydrolyzate, alcohols such as ethanol, and organic acids such as acetic acid, lactic acid and succinic acid can be used.

As the nitrogen source, various inorganic and organic ammonium salts such as ammonia, ammonium chloride, ammonium sulfate, ammonium carbonate and ammonium acetate, urea, other nitrogen-containing compounds, and nitrogen-containing organic substances such as meat extract, yeast extract, corn steep liquor and a soybean hydrolyzate can be used.

As the inorganic salts, dipotassium hydrogen phosphate, potassium dihydrogen phosphate, ammonium sulfate, sodium chloride, magnesium sulfate, calcium carbonate and the like can be used.

In addition to these, trace nutrient sources such as biotin, thiamine can be added, if necessary. These trace nutrient sources can be substituted with medium additives such as meat extract, yeast extract, corn steep liquor and casamino acid.

The culturing is carried out under aerobic conditions such as shaking culture or aeration agitation culture. Usually, the culture temperature is preferably from 20° C. to 42° C., and more preferably from 25° C. to 40° C. It is preferable that pH in the medium is kept at 5 to 9. The pH is adjusted by using inorganic or organic acid, an alkaline solution, urea, calcium carbonate, ammonia or the like. The culturing period of time is usually from 12 hours to 6 days. In addition, antibiotics such as ampicillin and tetracycline can be added to the medium during the culturing, if necessary.

When a microorganism transformed with a recombinant vector using an inducible promoter as its promoter is cultured, an inducer can be added to the medium, if necessary. For example, isopropyl-β-D-thiogalactopyranoside or the like can be added to the medium, when a microorganism transformed with a recombinant vector using lac promoter is cultured, or indole acrylate or the like when a microorganism transformed with a recombinant vector using trp promoter is cultured.

The production process of the polypeptide of the present invention includes a method in which the polypeptide is produced inside the host cell, a method in which the polypeptide is secreted into extracellular moiety of the host or a method in which the polypeptide is produced on the outer membrane of the host cell, and structure of the polypeptide to be expressed can be changed by selecting the host cell in response to the method to be employed.

When the polypeptide of the present invention is produced inside the host cell or on the outer membrane of the host cell, the polypeptide can be positively secreted into the extracellular moiety of the host cell in accordance with the method of Paulson et al. [*J. Biol. Chem.*, 264, 17619 (1989)], the method of Low et al. [*Proc. Natl. Acad. Sci. USA*, 86, 8227 (1989), *Genes Develop.*, 4, 1288 (1990)], or the methods described in Japanese Published Unexamined Patent Application No. 336963/93, WO 94/23021 and the like.

In addition, the production amount can also be increased according to a gene amplification system using a dihydrofolate reductase gene, in accordance with the method described in Japanese Published Unexamined Patent Application No. 227075/90.

In order to isolate and purify the polypeptide produced by the transformant of the present invention, general enzyme isolation purification methods can be used.

For example, when the polypeptide of the present invention is expressed inside cells in a soluble form, the cells are recovered by centrifugation after completion of the culturing and suspended in an aqueous buffer, and then a cell-free extract is obtained by disrupting the cells by a sonicator, French press, Manton Gaulin homogenizer, Dyno mill and the like. A purified sample can be prepared from the supernatant obtained by centrifuging the cell-free extract, by using enzyme isolation purification methods, namely methods including solvent extraction, salting out by ammonium sulfate, desalting, precipitation with organic solvent, anion exchange chromatography using a resin such as diethylaminoethyl (DEAE)-Sepharose, DIAION HPA-75 (manufactured by Mitsubishi Chemical), cation exchange chromatography using a resin such as S-Sepharose FF (manufactured by Pharmacia), hydrophobic chromatography using a resin such as Phenyl Sepharose, gel filtration using a molecular sieve, affinity chromatography, chromatofocusing, and electrophoresis such as isoelectric focusing, alone or in combination thereof.

In addition, when the polypeptide is expressed inside the cells forming an insoluble body, the insoluble body of polypeptide is recovered in the same manner after recovery of the cells, followed by disruption and centrifugation. The recovered insoluble body of polypeptide is solubilized with a protein denaturing agent. By diluting or dialyzing the solubilized liquid to thereby lower a concentration of the protein denaturing agent in the solubilized liquid, the polypeptide is returned to its normal three-dimensional structure. After this operation, a purified sample of the polypeptide can be obtained by the same isolation purification method as described above.

When the polypeptide of the present invention or a derivative thereof such as a polypeptide in which a sugar chain is added to the polypeptide is secreted into the extracellular moiety, the polypeptide or the polypeptide derivative can be recovered in a culture supernatant. That is, a purified sample can be obtained from a culture supernatant by obtaining the culture supernatant through the treatment of the culture with a method such as centrifugation similar to the above, and using the same isolation purification method as described above.

The polypeptide obtained in this manner includes the polypeptide of the above-mentioned (1), and more specific examples include a polypeptide in which a glutamic acid residue at position 64 from the N-terminal in the amino acid sequence of SEQ ID NO:1 is substituted with a lysine residue.

(5) Microorganism of the Present Invention

The microorganism of the present invention includes a microorganism which produces the polypeptide of the present invention, and it may be any microorganism, so long as it is a microorganism which can produce the polypeptide of the present invention, and it is preferably a microorganism belonging to a coryneform bacterium, more preferably a microorganism belonging to the genus *Corynebacterium*, the genus *Brevibacterium* or the genus *Microbacterium*, and most preferably *Corynebacterium glutamicum*, or the like.

The microorganism of the present invention can be obtained by transforming a host cell with the DNA of the present invention in accordance with a general method, and includes, for example, the transformant obtained in the above-mentioned (4).

In addition, the microorganism of the present invention includes a microorganism comprising the DNA of the present invention on the chromosomal DNA. The microorganism can be obtained by introducing a site-directed mutation into the glutamine synthetase 2 on the chromosomal DNA of a microorganism to be used as a host, using a general mutation treatment, gene replacement by recombinant DNA techniques, cell fusion, transduction or the like. The introduction of site-directed mutation can be carried out in accordance with the methods described in *Molecular Cloning*, 3rd edition, *Current Protocols in Molecular Biology, Proc. Natl. Acad. Sci. USA,* 79, 6409 (1982), *Gene*, 34, 316 (1985), *Nucleic Acids Research*, 13, 4431 (1985), *Proc. Natl. Acad. Sci. USA,* 82, 488 (1985) and the like.

In addition, a microorganism comprising the DNA of the present invention on the chromosome can also be prepared by substituting a DNA encoding the glutamine synthetase on the chromosomal DNA with the DNA of the present invention obtained by the method of the above-mentioned (3) using a homologous recombination method.

Specifically, the DNA of the present invention obtained by the method of the above-mentioned (3) is introduced into a microorganism in accordance with the method according to the above-mentioned (4), by introducing it into a plasmid which cannot perform autonomous replication in host cells and has an antibiotics-resistance marker gene and *Bacillus subtilis* levan sucrase gene sac B [*Mol. Microbiol.*, 6, 1195 (1992)].

Since the recombinant plasmid cannot autonomously replicate in host cells, a transformant in which the recombinant plasmid is integrated into the chromosome by a Campbell type homologous recombination can be obtained by selecting it based on the antibiotics-resistance presenting on the recombinant plasmid.

Next, a strain in which the glutamine synthetase 2 on the host chromosomal DNA is substituted with the DNA of the present invention can be obtained by selection based on the fact that the *Bacillus subtilis* levan sucrase to be integrated onto the chromosome together with the DNA of the present invention converts sucrose into a suicide substrate [*J. Bacteriol.*, 174, 5462 (1992)].

The gene replacement on the chromosome can be carried out by the above method, but other gene replacement method can also be used without limitation to the above-mentioned method, so long as it is a method which can substitute genes on the chromosome.

Other methods for preparing a microorganism comprising the DNA of the present invention on the chromosome include a cell fusion method and a transduction method. Examples include methods described in *Amino San Hakko* (*Amino Acid Fermentation*), edited by Hiroshi Aida et al., 1986, Gakkai Shuppan Center.

In addition, the microorganism of the present invention includes:
(i) a microorganism which has ability to produce a polypeptide comprising an amino acid sequence in which one or more amino acids are deleted, substituted or added in the amino acid sequence of LtsA derived from a microorganism belonging to a coryneform bacterium, and has lysozyme sensitivity,
(ii) the microorganism according to the above (i), wherein the polypeptide comprises an amino acid sequence in which an amino acid at a position corresponding to the amino acid at position 80 from the N-terminal in the amino acid sequence of SEQ ID NO:10 is an amino acid other than glycine,
(iii) the microorganism according to the above (ii), wherein the amino acid other than glycine is aspartic acid,
(iv) the microorganism according to the above (i), wherein the amino acid sequence of LtsA is the amino acid sequence of SEQ ID NO:10,
(v) the microorganism according to the above (iv), wherein the polypeptide comprises an amino acid sequence in which the amino acid at position 80 from the N-terminal in the amino acid sequence of SEQ ID NO:10 is an amino acid other than glycine, and
(vi) the microorganism according to the above (v), wherein the amino acid other than glycine is aspartic acid,
and which also comprises the DNA of the present invention, and the like.

The LtsA derived from a microorganism belonging to a coryneform bacterium can be obtained in the usual method using a DNA encoding LtsA, which can be obtained by the above-mentioned hybridization using a complementary strand of a DNA having the nucleotide sequence of SEQ ID NO:11, or a complementary strand of a DNA comprising a part of the DNA, as a probe, or by PCR using a primer DNA which can be designed from the nucleotide sequence of SEQ ID NO:11 and using the above-mentioned *Corynebacterium* chromosomal DNA as a template.

The LtsA derived from a microorganism belonging to a coryneform bacterium may be any LtsA, so long as it is a LtsA derived from the above-mentioned microorganism belonging to a coryneform bacterium, and it includes, for example, the LtsA described in EP 1108790 comprising the amino acid sequence of SEQ ID NO:10.

The polypeptide comprising an amino acid sequence in which one or more amino acids are deleted, substituted or added in the amino acid sequence of LtsA derived from a microorganism belonging to a coryneform bacterium can be constructed by a method similar to the above-mentioned method for constructing a polypeptide comprising an amino acid sequence in which one or more amino acids are deleted, substituted or added in the amino acid sequence of the glutamine synthetase 2 derived from a microorganism belonging to a coryneform bacterium. The number, position and kind of the deleted, substituted or added amino acids are the same as the case of the above-mentioned polypeptide comprising an amino acid sequence in which one or more amino acids are deleted, substituted or added in the amino acid sequence of the glutamine synthetase 2 derived from a microorganism belonging to a coryneform bacterium.

A coryneform bacterium which produces the polypeptide comprising an amino acid sequence in which one or more amino acids in the amino acid sequence of the LtsA derived from a microorganism belonging to a coryneform bacterium are deleted, substituted or added can be obtained by transforming a coryneform bacterium which produces a wild type LtsA and comprises the DNA of the present invention, with a DNA encoding the peptide that can be obtained by the above-mentioned method, and substituting the DNA encoding the peptide which can be obtained by the above-mentioned method for a DNA encoding the wild type LtsA according to a homologous recombination technique. By measuring that the coryneform microorganism shows lysozyme sensitivity and that a production amount of glutamine by the coryneform microorganism is larger than a production amount by the coryneform bacterium before introduction of LtsA mutation, it can be confirmed that the coryneform bacterium is the microorganism of the present invention.

The coryneform bacterium which produces the polypeptide comprising an amino acid sequence in which one or more amino acids in the amino acid sequence of the LtsA derived from a microorganism belonging to a coryneform bacterium are deleted, substituted or added shows lysozyme sensitivity means that, when the coryneform bacterium is cultured using a medium containing maximum concentration of lysozyme by which the coryneform bacterium which produces wild type LtsA before LtsA substitution, its growth rate is slower than the growth rate when the coryneform bacterium which produces wild type is cultured using the medium.

In the microorganism of the present invention in the above-mentioned (ii) or (iii), the amino acid at a position corresponding to the amino acid at position 80 from the N-terminal in the amino acid sequence of SEQ ID NO:10 in the LtsA derived from a microorganism belonging to a coryneform bacterium means an amino acid at a position corresponding to the amino acid at position 80 from the N-terminal in the amino acid sequence of SEQ ID NO:10 in the amino acid sequence of the LtsA derived from a microorganism belonging to a coryneform bacterium, when the homology of the amino acid sequence of the LtsA derived from a microorganism belonging to a coryneform bacterium with the amino acid sequence of SEQ ID NO:10 is calculated using an analyzing program, such as the above-mentioned BLAST and FASTA, and parameters and both of the sequences are aligned.

The amino acid other than glycine may be any amino acid, so long as it is an amino acid other than glycine, but is preferably an amino acid selected from alanine, valine, leucine, isoleucine, cysteine, methionine, tryptophan, phenylalanine, proline, lysine, histidine, arginine, aspartic acid, asparagine, glutamine, serine, threonine, tyrosine and glutamic acid, and more preferably aspartic acid.

The microorganism of the present invention in the above-mentioned (ii) or (iii) can be obtained by constructing a DNA in which a codon encoding an amino acid at a position corresponding to the amino acid at position 80 from the N-terminal in the amino acid sequence of SEQ ID NO:10 in the LtsA derived from a microorganism belonging to a coryneform bacterium is substituted with a codon encoding an amino acid other than glycine using the above-mentioned site-directed mutagenesis, using this DNA to transform a coryneform bacterium which produces a wild type LtsA and comprises the DNA of the present invention, and substituting the DNA which can be obtained by the above-mentioned method by a DNA encoding the wild type LtsA according to a homologous recombination technique. By measuring that the coryneform microorganism shows lysozyme sensitivity and that the production amount of glutamine by the coryneform microorganism is larger than the production amount by the coryneform bacterium before introducing LtsA, it can be confirmed that the coryneform bacterium is the microorganism of the present invention.

The polypeptide comprising an amino acid sequence in which one or more amino acids are deleted, substituted or added in the amino acid sequence of SEQ ID NO:10 in the above-mentioned (iv) can be constructed using a DNA encoding the amino acid sequence of SEQ ID NO:10, in the same manner as the above-mentioned method for constructing a polypeptide comprising an amino acid sequence in which one or more amino acids are deleted, substituted or added in the amino acid sequence of the glutamine synthetase 2 derived from a microorganism belonging to a coryneform bacterium. The number, position and kind of the amino acids to be deleted, substituted or added are described above.

The coryneform bacterium which comprises an amino acid sequence in which one or more amino acids are deleted, substituted or added in the amino acid sequence of SEQ ID NO:10 and also produces the polypeptide comprising the amino acid sequence as only one LtsA produced inside the cells can be obtained by transforming a coryneform bacterium which produces the wild type LtsA and also comprises the DNA of the present invention with a DNA encoding the polypeptide which can be obtained by the above-mentioned method, and substituting the DNA encoding the polypeptide which can be obtained by the above-mentioned method and the DNA encoding the wild type LtsA according to a homologous recombination technique. By determining by measurement that the coryneform microorganism shows lysozyme sensitivity and that the production amount of glutamine by the coryneform microorganism is larger than the production amount by the coryneform bacterium before introducing LtsA, it can be confirmed that the coryneform bacterium is the microorganism of the present invention.

The microorganism of the present invention in the above-mentioned (v) or (vi) can be obtained using a DNA encoding the amino acid sequence of SEQ ID NO:10 and using a DNA in which the codon encoding a glycine residue at position 80 from the N-terminal in the amino acid sequence of SEQ ID NO:1 is substituted with a codon encoding an amino acid other than a glycine residue according to the above-mentioned site-directed mutagenesis. The amino acid includes the above-mentioned amino acid other than glycine.

The microorganism of the present invention in the above-mentioned (v) or (vi) can be obtained by constructing a DNA in which the codon encoding glycine at position 80 from the N-terminal in the amino acid sequence of SEQ ID NO:10 is substituted with a codon encoding an amino acid other than glycine using the above-mentioned site-directed mutagenesis, transforming a coryneform bacterium which produces a wild type LtsA and also comprises the DNA of the present invention with the mutated DNA, and substituting the DNA which can be obtained by the above-mentioned method for a DNA encoding the wild type LtsA according to a homologous recombination technique. By determining by measurement that the coryneform microorganism shows lysozyme sensitivity and that the production amount of glutamine by the coryneform microorganism is larger than the production amount by the coryneform bacterium before introducing LtsA, it can be confirmed that the coryneform bacterium is the microorganism of the present invention.

Also, in the microorganisms of the above-mentioned (i) to (vi), the microorganism of the present invention can also be constructed by introducing a mutation of LtsA into a coryneform bacterium as described above and then providing the ability to produce of the polypeptide of the present invention.

(6) Production of L-Glutamine

L-Glutamine can be obtained by culturing the transformant obtained in the above-mentioned (4) or the microorganism of the present invention obtained in the above-mentioned (5) in a medium to thereby form and accumulating L-glutamine in the culture, and recovering L-glutamine from the culture.

Culturing of the microorganism can be carried out by a usual culturing method of a microorganism having ability to produce L-glutamine.

As the medium, each of a natural medium or a synthetic medium can be used, so long as it contains a carbon source, a nitrogen source, inorganic salts and the like in appropriate amounts.

The carbon source may be any substance which can be assimilated by the microorganism of the present invention, and sugars such as glucose, fructose, sucrose, maltose and a starch hydrolyzate, alcohols such as ethanol, and organic acids such as acetic acid, lactic acid and succinic acid and the like can be used.

As the nitrogen source, various inorganic and organic ammonium salts such as ammonia, ammonium chloride, ammonium sulfate, ammonium carbonate and ammonium acetate, urea, other nitrogen-containing compounds, and nitrogen-containing organic substances such as meat extract, yeast extract, corn steep liquor and a soybean hydrolyzate and the like can be used.

As the inorganic salts, dipotassium hydrogen phosphate, potassium dihydrogen phosphate, ammonium sulfate, sodium chloride, magnesium sulfate, calcium carbonate and the like can be used.

In addition to these, trace nutrient sources such as biotin, thiamine, nicotinamide and nicotinic acid can be added, if necessary. These trace nutrient sources can be substituted with medium additives such as meat extract, yeast extract, corn steep liquor and casamino acid.

The culturing is carried out under aerobic conditions such as shaking culture or submerged aeration agitation culture. Usually, the culture temperature is preferably from 20° C. to 42° C., and more preferably from 30° C. to 40° C. It is preferable that pH in the medium is kept at a neutral region of 5 to 9. The pH is adjusted by using inorganic or organic acid, an alkaline solution, urea, calcium carbonate, ammonia, a pH buffer or the like.

The culturing period is generally from 12 hours to 6 days, and L-glutamine is formed and accumulated in the culture.

After completion of the culturing, L-glutamine can be recovered from the culture liquid obtained by removing precipitates such as cells according to conventionally known methods in combination, such as an activated carbon treatment and an ion exchange resin treatment.

Examples of the present invention are shown below, but the present invention is not limited to these examples.

Example 1

Preparation of Plasmid pCglnA2 for Gene Replacement

A DNA encoding a polypeptide having an amino acid sequence in which the amino acid at position 64 from the N-terminal in the amino acid sequence of SEQ ID NO:1 was substituted with lysine (Glu64Lys) was obtained according to a site-directed mutagenesis using PCR [*Molecular Cloning*, 3rd edition] in the following manner.

Firstly, a chromosomal DNA of *Corynebacterium glutamicum* strain ATCC 13032, which is a wild type strain, was prepared in accordance with the method of Saito et al. [*Biochim. Biophys. Acta*, 72, 619 (1963)].

Next, using the chromosomal DNA as a template, PCR was carried out using Pyrobest DNA polymerase (manufactured by Takara Bio), the buffer attached thereto and the primers described below. As primers used in the PCR, a DNA fragment consisting of a nucleotide sequence in which, in a region encoding the glutamine synthetase 2 of SEQ ID NO:2, a region consisting of 21 nucleotides (a nucleotide sequence at positions 180 to 200 from the 5'-terminal in the nucleotide sequence of SEQ ID NO:2, and a nucleotide sequence at positions 680 to 700 from the 5'-terminal in the nucleotide sequence of SEQ ID NO:3) containing a region encoding glutamic acid at position 64 from the N-terminal in the amino acid sequence of SEQ ID NO:1 (a region of positions 190 to 192 from the 5'-terminal in the nucleotide sequence of SEQ ID NO:2, gaa) was substituted with a codon (aaa) encoding lysine, based on the nucleotide sequence information on a DNA encoding the *Corynebacterium glutamicum*-derived glutamine synthetase 2 described in EP 1108790, and a DNA fragment consisting of a nucleotide sequence of 21 nucleotides of SEQ ID NO:6 as a complementary sequence thereof were synthesized in accordance with a general method.

In addition, a DNA fragment in which a tag sequence containing a BamHI recognition sequence was added to the nucleotide sequence at positions 167 to 186 from the 5'-terminal in the nucleotide sequence of SEQ ID NO:3 was synthesized, and the nucleotide sequence is shown in SEQ ID NO:4.

A DNA fragment in which a tag sequence containing a BamHI recognition sequence was added to a complementary sequence of the nucleotide sequence at positions 1185 to 1204 from the 5'-terminal in the nucleotide sequence of SEQ ID NO:3 was synthesized, and the nucleotide sequence is shown in SEQ ID NO:7.

Using the DNA fragment having the nucleotide sequence of SEQ ID NO:4 and a DNA fragment having the nucleotide sequence of SEQ ID NO:6 as primers, or using a DNA fragment having the nucleotide sequence of SEQ ID NO:5 and the DNA fragment having the nucleotide sequence of SEQ ID NO:7 as primers, two kinds of PCR were respectively carried out using Pyrobest DNA polymerase (manufactured by Takara Bio) and the buffer attached thereto by using the thus obtained chromosomal DNA as a template.

The amplified products of about 0.5 kb obtained by respective PCR (a DNA fragment corresponding to the nucleotide sequence at positions 167 to 700 from the 5'-terminal in the nucleotide sequence of SEQ ID NO:3, and a DNA fragment corresponding to that at positions 167 to 700) were subjected to agarose gel electrophoresis and then extracted and purified using GENECLEAN Kit (manufactured by BIO 101).

In addition, PCR was carried out using both of the purified products as a template and using the DNA fragment having the nucleotide sequence of SEQ ID NO:4 and the DNA fragment having the nucleotide sequence of SEQ ID NO:7 as primers. By this PCR, about 1.0 kb of a DNA fragment in which a codon (gaa) encoding glutamic acid at position 64 from the N-terminal in the amino acid sequence of SEQ ID NO:1 was substituted with a codon (aaa) encoding lysine was obtained. The thus obtained DNA fragment of about 1.0 kb was treated with BamHI, subjected to agarose gel electrophoresis and then extracted and purified using GENECLEAN Kit (manufactured by BIO 101).

The DNA fragment was inserted into a plasmid pESB30. The pESB30 is a plasmid in which a 2.6 kb PstI DNA fragment [*Mol. Microbiol.*, 6, 1195 (1992)] containing a *Bacillus subtilis*-derived levan sucrase gene sacB was ligated to the PstI cleavage site of a vector pHSG299 [*Gene*, 61, 63 (1987)] which contains a kanamycin resistance gene. Specifically, the pESB30 was digested with BamHI (manufactured by Takara Bio), treated with an alkaline phosphatase (manufactured by Takara Bio) and then subjected to agarose gel electrophoresis, and the BamHI-treated fragment of pESB30 was extracted and purified using GENECLEAN Kit (manufactured by BIO 101). By mixing this pESB30 fragment with the BamHI-treated DNA fragment of about 1.0 kb obtained in the above, ligation thereof was carried out using Ligation Kit ver 1 (manufactured by Takara Bio). Using the thus obtained reaction product, *Escherichia coli* DH5α (manufactured by TOYOBO) was transformed in accordance with the conventional method (*Molecular Cloning*, 3rd edition).

A transformant was selected by culturing the strain on an LB agar medium [a medium which contains 10 g of bacto tryptone (manufactured by Difco), 5 g of yeast extract (manufactured by Difco), 10 g of sodium chloride and 16 g of bacto agar (manufactured by Difco) in 1 liter of water, and was adjusted to pH 7.0] containing 20 μg/ml of kanamycin. The transformant was cultured overnight in an LB medium containing 20 μg/ml of kanamycin, and a plasmid was prepared from the thus obtained culture by an alkaline SDS method (*Molecular Cloning*, 3rd edition).

By a restriction enzyme digestion analysis, it was confirmed that the plasmid is a plasmid having a structure in which the DNA fragment of about 1.0 kb obtained in the above was inserted into pESB30. This plasmid was named pCglnA2.

Example 2

Construction of pGlnA2 for Gene Expression

A DNA encoding a polypeptide having an amino acid sequence in which glutamic acid at position 64 from the N-terminal in the amino acid sequence of SEQ ID NO:1 was substituted with lysine (Glu64Lys) was obtained in the same manner as in Example 1.

From a chromosomal DNA of *Corynebacterium glutamicum* strain ATCC 13032, which is a wild type strain, a DNA fragment in which a tag sequence containing a BamHI recognition sequence was added to a nucleotide sequence positioned at an upstream of the 5'-terminal side in a nucleotide sequence encoding a glutamine synthetase 2 (the nucleotide sequence at positions 1 to 20 from the 5'-terminal in the nucleotide sequence of SEQ ID NO:3) and a DNA fragment in which a tag sequence containing a BamHI recognition sequence was added to a complementary sequence of a nucleotide sequence positioned at the 3'-terminal side thereof (the nucleotide sequence at positions 1825 to 1844 from the 5'-terminal in the nucleotide sequence of SEQ ID NO:3) were synthesized, and their nucleotide sequences are shown in SEQ ID NO:8 and SEQ ID NO:9, respectively.

Using the DNA fragment having the nucleotide sequence of SEQ ID NO:8 and the DNA fragment having the nucleotide sequence of SEQ ID NO:6 as primers, or using the DNA fragment having the nucleotide sequence of SEQ ID NO:5 and the DNA fragment having the nucleotide sequence of SEQ ID NO:9 as primers, two kinds of PCR were respectively carried out using Pyrobest DNA polymerase (manufactured by Takara Bio) and the buffer attached thereto by using the chromosomal DNA of ATCC 13032 as a template.

The amplified product of about 0.7 kb (a DNA fragment corresponding to the nucleotide sequence at position 1 to 700 from the 5'-terminal in the nucleotide sequence of SEQ ID NO:3) and the amplified product of about 1.1 kb (a DNA fragment corresponding to the nucleotide sequence at positions 680 to 1844 from the 5'-terminal in the nucleotide sequence of SEQ ID NO:3), obtained by the respective PCR, were subjected to agarose gel electrophoresis and extracted and purified using GENECLEAN Kit (manufactured by BIO 101).

In addition, PCR was carried out using both of the purified products as a template and using the DNA fragment having the nucleotide sequence of SEQ ID NO:8 and the DNA fragment having the nucleotide sequence of SEQ ID NO:9 as primers. By this PCR, about 1.9 kb of a DNA fragment having the promoter sequence existing in the upstream of the 5'-terminal side of glutamine synthetase 2 and, in SEQ ID NO:2, a sequence in which a codon (gaa) encoding glutamic acid at position 64 from the N-terminal in the amino acid sequence of SEQ ID NO:1 was substituted with a codon (aaa) encoding lysine was obtained. This DNA fragment of about 1.9 kb was treated with BamHI (manufactured by Takara Bio), subjected to agarose gel electrophoresis and then extracted and purified using GENECLEAN Kit (manufactured by BIO 101). The pCS299P (WO 00/63388) was digested with BamHI (manufactured by Takara Bio), treated with an alkaline phosphatase (manufactured by Takara Bio) and then subjected to agarose gel electrophoresis, and the pCS299P fragment was extracted and purified using GENECLEAN Kit (manufactured by BIO 101).

The BamHI-treated DNA fragment of about 1.9 kb obtained above was cloned into this pCS299P fragment in the same manner as in Example 1.

By carrying out a restriction enzyme digestion analysis, it was confirmed that the plasmid is a plasmid having a structure in which the DNA fragment of about 1.9 kb obtained above was inserted into pCS299P. This plasmid was named pGlnA2.

Example 3

Preparation of Plasmid pCltsA for Gene Replacement

A DNA encoding a polypeptide having an amino acid sequence in which glycine at position 80 from the N-terminal of the amino acid sequence of the lysozyme sensitivity-related polypeptide of SEQ ID NO:10 was substituted with asparagine (Gly80Asp) was obtained in the same manner as in Example 1. It was reported that the lysozyme sensitivity is given by the introduction of the same mutation (*BMC Biotechnol.*, 9, 1 (2001)).

A DNA fragment in which a tag sequence containing a BamHI recognition sequence was added to the nucleotide sequence at positions 1 to 20 from the 5'-terminal in the nucleotide sequence of SEQ ID NO:12 and a DNA fragment in which a tag sequence containing a BamHI recognition sequence was added to a complementary sequence of the nucleotide sequence at positions 981 to 1000 from the 5'-terminal in the nucleotide sequence of SEQ ID NO:12, which is a peripheral region of the DNA encoding LtsA, in a chromosomal DNA of *Corynebacterium glutamicum* wild strain ATCC 13032, were synthesized, and their nucleotide sequences are shown in SEQ ID NO:13 and SEQ ID NO:16, respectively. A DNA fragment consisting of the nucleotide sequence of SEQ ID NO:15 in which, in a region consisting of 21 nucleotides (the nucleotide sequence at positions 229 to 249 from the 5'-terminal in the nucleotide sequence of SEQ ID NO:11, and the nucleotide sequence at positions 491 to 511 from the 5'-terminal in the nucleotide sequence of SEQ ID NO:12), among the region encoding the LtsA of SEQ ID NO:11, containing a codon encoding the glycine at position 80 from the N-terminal in the amino acid sequence of the LtsA of SEQ ID NO:10 (the nucleotide sequence at positions 238 to 240 from the 5'-terminal in the nucleotide sequence of SEQ ID NO:11, ggt), the glycine was substituted with a codon (gat) encoding aspartic acid, and a DNA fragment having the nucleotide sequence of 21 nucleotides of SEQ ID NO:14, were synthesized in accordance with a general method.

Using the DNA fragment having the nucleotide sequence of SEQ ID NO:13 and the DNA fragment having the nucleotide sequence of SEQ ID NO:14 as primers or using the DNA fragment having the nucleotide sequence of SEQ ID NO:15 and the DNA fragment having the nucleotide sequence of SEQ ID NO:16 as primers, two kinds of PCR were respectively carried out using the chromosomal DNA of the strain of ATCC 13032 as a template and using Pyrobest DNA polymerase (manufactured by Takara Bio) and the buffer attached thereto.

The amplified products of about 0.5 kb obtained by respective PCR (a DNA fragment corresponding to the nucleotide sequence at positions 1 to 511 from the 5'-terminal in the nucleotide sequence of SEQ ID NO:12, and a DNA fragment corresponding to the nucleotide sequence at positions 491 to 1000 from the 5'-terminal in the nucleotide sequence of SEQ ID NO:12) were subjected to agarose gel electrophoresis and extracted and purified using GENECLEAN Kit (manufactured by BIO 101).

In addition, PCR was carried out using both of the purified products as a template and using the DNA fragment having the nucleotide sequence of SEQ ID NO:13 and the DNA fragment having the nucleotide sequence of SEQ ID NO:16 as primers. By this PCR, about 1.0 kb of a DNA fragment in which a region encoding the codon (ggt) encoding glycine at position 80 from the N-terminal in the amino acid sequence of SEQ ID NO:10 was substituted with the codon (gat) encoding aspartic acid was obtained. This DNA fragment of about 1.0 kb was treated with BamHI (manufactured by Takara Bio) and cloned into pESB30 in the same manner as in Example 1, and the plasmid was named pCltsA.

Example 4

Construction of L-Glutamine Producing Strain Having the DNA of the Present Invention Using the plasmid pCglnA2 prepared in the above-mentioned Example 1, a mutation in which glutamic acid at position 64 from the N-terminal in the amino acid sequence of SEQ ID NO:1 was substituted with lysine (Glu64Lys) was introduced into a gene encoding a glutamine synthetase 2 in a chromosomal DNA of *Corynebacterium glutamicum* ATCC 13032 by a gene replacement method.

Introduction of mutation by a gene replacement method into the gene encoding a glutamine synthetase 2 in a chromosomal DNA of ATCC 13032 was carried out by the following recombination method in twice. Firstly, based on the fact that the plasmid pCglnA2 prepared in the above cannot autonomously replicate in the cells of coryneform bacteria, a strain in which this plasmid was integrated by a homologous recombination into the *Corynebacterium glutamicum* ATCC 13032 was selected by the following method.

Specifically, ATCC 13032 was transformed with the plasmid by electroporation in accordance with the method of Rest, et al. [*Appl. Microbiol. Biotechnol.*, 52, 541 (1999)], and kanamycin-resistant strains were selected. When the structure of the chromosome obtained from one strain of the thus selected kanamycin-resistant strains was examined by the Southern hybridization (*Molecular Cloning*, 3rd edition), it was confirmed that the plasmid was integrated into the chromosome by a Campbell type homologous recombination. In such a strain, wild type and mutation type glutamine synthetase 2 genes are present contiguously on the chromosome, and a second homologous recombination is apt to occur between them.

The transformant (first recombinant) was spread on a SUC agar medium [a medium which contains 100 g of sucrose, 7 g of meat extract, 10 g of peptone, 3 g of sodium chloride, 5 g of Yeast Extract (manufactured by Difco) and 18 g of Bacto-Agar (manufactured by Difco) in 1 liter of water, and is adjusted to pH 7.2] and cultured at 30° C. for 1 day to select grown colonies. Since a strain having the sacB gene is present converts sucrose into a suicide substrate, it cannot grow on this medium [*J. Bacteriol.*, 174, 5462 (1992)]. On the other hand, the suicide substrate is not formed by a strain in which the sacB gene was deleted because of the second homologous recombination between the wild type and mutation type glutamine synthetase 2 genes which are present contiguously on the chromosome, so that it can grow on this medium. During this second homologous recombination, either the wild type gene or the mutation type gene was deleted together with sacB. In this case, it can be considered that the gene was replaced with the mutation type occurred in the strain in which the wild type was deleted together with sacB.

The chromosomal DNA of the second transformant obtained in this manner was prepared by the method of Saito et al. [*Biochim. Biophys. Acta*, 72, 619 (1963)], and using the chromosomal DNA as a template and using a DNA fragment having the nucleotide sequence of SEQ ID NO:4 and a DNA fragment having the nucleotide sequence of SEQ ID NO:7 as primers, PCR was carried out by using Pyrobest DNA polymerase (manufactured by Takara Bio) and the buffer attached thereto. By determining nucleotide sequences of these PCR products by the usual method, it was judged whether the glutamine synthetase 2 gene on the chromosomal DNA of the second recombinant was the wild type or the mutated type. As a result, a strain GS2 was obtained, which is a second recombinant having a mutation of replacing the glutamic acid at position 64 from the N-terminal in the amino acid sequence of SEQ ID NO:1 with lysine (Glu64Lys), in the gene encoding the glutamine synthetase 2 on the chromosomal DNA.

In addition to the strain GS2, a strain GLA2 was obtained by introducing a mutation in which the glycine at position 80 from the N-terminal of the amino acid sequence of SEQ ID NO:10 was substituted with aspartic acid (Gly80Asp) into the LtsA gene on the chromosomal DNA, in the same manner as described in the above using pCltsA. The same operation was carried out, except that the strain GS2 was used as a host and pCltsA was used as a plasmid for replacement. The chromosomal DNA of the thus obtained second transformant was prepared by the method of Saito et al. [*Biochim. Biophys. Acta*, 72, 619 (1963)], and PCR was carried out using the chromosomal DNA as a template and using a DNA fragment having the nucleotide sequence of SEQ ID NO:13 and a DNA fragment having the nucleotide sequence of SEQ ID NO:16 as primers, by using Pyrobest DNA polymerase (manufactured by Takara Bio) and the buffer attached thereto. By determining nucleotide sequences of these PCR products by the usual method, whether the LtsA gene on the chromosomal DNA of the second recombinant was the wild type or mutation type was judged. As a result, a strain GLA2 was obtained, which was a second recombinant having a mutation of replacing the glycine at position 80 from the N-terminal in the amino acid sequence of SEQ ID NO:10 with aspartic acid (Gly80Asp), in the gene encoding the LtsA on the chromosomal DNA.

In addition, a strain ATCC 13032/pGlnA2 and a strain ATCC 13032/pCS299P were obtained by transforming with the pGlnA2 prepared in Example 2 or the pCS299P as a control into the ATCC 13032 by the electroporation.

Example 5

L-Glutamine Production Test by Glutamine Synthetase 2 Mutant Strains

Each of the obtained strain GS2, strain GLA2, strain ATCC 13032/pGlnA2, strain ATCC 13032/pCS299P and the parent strain ATCC 13032 was cultured at 30° C. for 24 hours using a BYG agar medium [a medium which contains 10 g of glucose, 7 g of meat extract, 10 g of peptone, 3 g of sodium chloride, 5 g of yeast extract (manufactured by Difco) and 18 g of Bacto-Agar (manufactured by Difco) in 1 liter of water and was adjusted to pH 7.2], and each strain was respectively inoculated into a test tube containing 6 ml of a seed culture medium [a medium prepared by containing 50 g of glucose, 20 g of bouillon, 5 g of ammonium sulfate, 5 g of urea, 2 g of potassium dihydrogen phosphate, 0.5 g of magnesium sulfate heptahydrate, 1 mg of iron sulfate heptahydrate, 0.4 mg of cupper sulfate pentahydrate, 0.9 mg of zinc sulfate heptahydrate, 0.07 mg of manganese chloride tetrahydrate, 0.01 mg of disodium tetraborate, 0.04 mg of hexaammonium heptamolybdate, 0.5 mg of thiamine hydrochloride and 0.1 mg of biotin in 1 liter of water, adjusting to pH 7.2 and then adding 10 g of calcium carbonate] and cultured at 30° C. for 12 hours to 16 hours.

Each of the thus obtained seed cultures was inoculated, at an inoculum size of 10%, into a 300 ml capacity conical flask with baffles containing 30 ml of a main culture medium [a medium prepared by containing 50 g of glucose, 2 g of urea, 20 g of ammonium sulfate, 0.5 g of potassium dihydrogen phosphate, 0.5 g of dipotassium hydrogen phosphate, 0.5 g of magnesium sulfate heptahydrate, 2 mg of iron sulfate heptahydrate, 2.5 mg of manganese sulfate pentahydrate, 0.5 mg of thiamine hydrochloride and 0.1 mg or 0.001 mg of biotin in 1 liter of water, adjusting to pH 7.2 and then adding 20 g of calcium carbonate] and cultured for 16 to 18 hours under conditions at 30° C. and 220 rpm before the sugar was not completely consumed.

After completion of the culturing, the cells were removed from the culture by centrifugation, and amounts of the L-glutamine and L-glutamic acid accumulated in the supernatant were respectively determined by high performance liquid chromatography (HPLC). In addition, respective amounts of the cells after completion of the culturing were measured as absorbance at 660 nm (OD660) of culture. The results are shown in Table 1.

TABLE 1

| Strain | Biotin concentration (mg/l) | Glutamine (g/l) | Glutamic acid (g/l) | OD660 |
|---|---|---|---|---|
| ATCC 13032 | 0.1 | 0.0 | 0.0 | 45.2 |
| GS2 | 0.1 | 0.2 | 0.0 | 49.2 |
| ATCC 13032/pCS299P | 0.1 | 0.0 | 0.0 | 44.3 |
| ATCC 13032/pGlnA2 | 0.1 | 0.3 | 0.0 | 45.6 |
| GLA2 | 0.1 | 4.6 | 0.9 | 40.2 |
| ATCC 13032 | 0.001 | 0.7 | 2.5 | 38.9 |
| GS2 | 0.001 | 2.3 | 0.0 | 38.9 |
| ATCC 13032/pCS299P | 0.001 | 1.1 | 3.1 | 32.2 |
| ATCC 13032/pGlnA2 | 0.001 | 6.8 | 2.4 | 34.4 |

As is apparent from Table 1, L-glutamine production efficiency of the strain GS2 and strain ATCC 13032/pGlnA2 having the DNA of the present invention was significantly improved in comparison with the parent strain. In addition, the glutamine production efficiency was improved without restricting biotin by introducing a mutation into the LtsA gene.

INDUSTRIAL APPLICABILITY

According to the present invention, a novel L-glutamine production process can be provided.

SEQUENCE LISTING FREE TEXT

SEQ ID NO:4-Description of artificial sequence: synthetic DNA
SEQ ID NO:5-Description of artificial sequence: synthetic DNA
SEQ ID NO:6-Description of artificial sequence: synthetic DNA
SEQ ID NO:7-Description of artificial sequence: synthetic DNA
SEQ ID NO:8-Description of artificial sequence: synthetic DNA
SEQ ID NO:9-Description of artificial sequence: synthetic DNA
SEQ ID NO:13-Description of artificial sequence: synthetic DNA
SEQ ID NO:14-Description of artificial sequence: synthetic DNA
SEQ ID NO:15-Description of artificial sequence: synthetic DNA
SEQ ID NO:16-Description of artificial sequence: synthetic DNA

The invention claimed is:

1. A isolated DNA encoding a modified polypeptide having glutamine synthetase 2 activity, wherein the polypeptide comprises the amino acid sequence of SEQ ID NO: 1, wherein the modification is the substitution of glutamic acid at position 64 from the N-terminal of SEQ ID NO: 1 (corresponding to codon or nucleotides 190-192 of SEQ ID NO: 2) with an amino acid other than glutamic acid and further comprising deletion, substitution or addition of 1-20 amino acids in the sequence of SEQ ID NO: 1, wherein said DNA when expressed in Coryneform bacterium as a host cell results in increased L-glutamine production as compared unmodified wild type Coryneform bacterium.

2. The isolated DNA of claim 1, wherein the codon encoding the glutamic amino acid encodes lysine.

3. The isolated DNA of claim 1 or 2, wherein the coryneform bacterium belongs to the genus *Corynebacterium, Brevibacterium* or *Mycobacterium*.

4. An isolated DNA encoding a modified polypeptide having glutamine synthetase 2 activity which is at least 95% identical to the nucleotide sequence of SEQ ID NO:2, and comprises a nucleotide sequence in which a region corresponding to the nucleotide sequence at positions 190 to 192 from the 5'-terminal in the nucleotide sequence of SEQ ID NO:2 is a codon encoding a basic amino acid, wherein a production amount of L-glutamine in a transformant obtained by introducing the DNA into a wild type coryneform bacterium is larger than that of the wild type coryneform bacterium.

5. The isolated DNA of claim 4, wherein the codon encoding the basic amino acid encodes lysine.

6. An isolated microorganism transformed with the isolated recombinant DNA of claim 1 or 4.

7. An isolated microorganism which comprises, on its chromosomal DNA, the isolated DNA of claim 1 or 4.

8. The isolated microorganism of claim 6, which has an ability of producing a polypeptide comprising an amino acid sequence in which from one to twenty amino acids are deleted, substituted or added in the amino acid sequence of LtsA obtained from a microorganism belonging to a coryneform bacterium, and has lysozyme sensitivity, wherein the polypeptide comprises an amino acid sequence in which an amino acid at a position corresponding to the amino acid at position 80 from the N-terminal in the amino acid sequence of SEQ ID NO:10 is aspartic acid.

9. The isolated microorganism according to of claim 7, wherein the amino acid sequence of LtsA is SEQ ID NO:10.

10. The isolated microorganism of claim 6, wherein the microorganism belongs to the genus *Corynebacterium, Brevibacterium* or *Mycobacterium*.

11. The isolated microorganism of claim 10, wherein the microorganism is *Corynebacterium glutamicum*.

12. A process for producing L-glutamine, which comprises culturing the microorganism of claim 6 in a medium to form and accumulate L-glutamine in a culture, and recovering L-glutamine from the culture.

* * * * *

UNITED STATES PATENT AND TRADEMARK OFFICE
CERTIFICATE OF CORRECTION

PATENT NO. : 8,067,211 B2
APPLICATION NO. : 12/159156
DATED : November 29, 2011
INVENTOR(S) : Hayashi et al.

It is certified that error appears in the above-identified patent and that said Letters Patent is hereby corrected as shown below:

COLUMN 4:

Line 46, "bacterium." should read --bacterium,--.

COLUMN 6:

Line 6, "is" should read --are--.

COLUMN 8:

Line 26, "before the sugar is not com-" should be deleted; and

Line 27, "pletely consumed" should read --without completely consuming the sugar--.

COLUMN 11:

Line 51, "YS-3,4-" should read --YS-314- --.

COLUMN 12:

Line 13, "phenylalaninc," should read --phenylalanine,--;

Line 14, "linc," should read --line,--.

COLUMN 15:

Line 53, "that" should read --which--.

COLUMN 23:

Line 16, "presenting" should read --present--.

COLUMN 24:

Line 6, "a LtsA" should read --an LtsA--; and

Line 49, "added shows" should read --added, showing--.

COLUMN 26:

Line 32, "accumulating" should read --accumulate--; and

Line 33, "recovering" should read --recover--.

Signed and Sealed this
Third Day of April, 2012

David J. Kappos
*Director of the United States Patent and Trademark Office*

CERTIFICATE OF CORRECTION (continued)
U.S. Pat. No. 8,067,211 B2

COLUMN 31:

Line 16, "in" should be deleted;

Line 17, "in the" should read --as--;

Line 41, "is" should be deleted; and

Line 52, "occurred" should read --occurring--.

COLUMN 32:

Line 52, "cupper" should read --copper--; and

Line 62, "containing" should read --combining--.

COLUMN 33:

Line 3, "before the sugar was not" should be deleted; and

Line 4, "completely consumed" should read --without completely consuming the sugar--.

COLUMN 57:

Line 48, "A" should read --An--.

COLUMN 59:

Line 4, "according to of claim 7," should read --of claim 8,--.